(12) United States Patent
Mumaw et al.

(10) Patent No.: US 11,497,570 B2
(45) Date of Patent: Nov. 15, 2022

(54) INDUCTIVELY POWERED END OF LIFE INDICATORS FOR ROBOTIC SURGICAL INSTRUMENTS

(71) Applicant: Ethicon LLC, Guaynabo, PR (US)

(72) Inventors: Daniel Mumaw, Liberty Township, OH (US); Niko Murrell, Blue Ash, OH (US); James Hoffmaster, Cincinnati, OH (US); John A. Hibner, Mason, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 718 days.

(21) Appl. No.: 16/395,710

(22) Filed: Apr. 26, 2019

(65) Prior Publication Data

US 2020/0337790 A1 Oct. 29, 2020

(51) Int. Cl.
*A61B 34/30* (2016.01)
*A61B 34/37* (2016.01)
*A61B 34/00* (2016.01)
*A61B 90/30* (2016.01)
*A61B 90/00* (2016.01)
*A61B 17/00* (2006.01)
*H02J 7/02* (2016.01)

(52) U.S. Cl.
CPC .............. *A61B 34/37* (2016.02); *A61B 34/71* (2016.02); *A61B 90/30* (2016.02); *A61B 90/36* (2016.02); *A61B 2017/00477* (2013.01); *A61B 2017/00734* (2013.01); *A61B 2090/309* (2016.02); *H02J 7/025* (2013.01)

(58) Field of Classification Search
CPC ......... A61B 34/00; A61B 34/37; A61B 34/71; A61B 90/30; A61B 34/30
See application file for complete search history.

(56) References Cited

U.S. PATENT DOCUMENTS

| 5,304,115 | A | * | 4/1994 | Pflueger | ........... | A61B 17/22012 |
| | | | | | | 606/169 |
| 6,331,181 | B1 | * | 12/2001 | Tierney | ................... | A61B 34/37 |
| | | | | | | 606/130 |
| 8,672,922 | B2 | * | 3/2014 | Loh | ........................ | A61B 34/30 |
| | | | | | | 606/1 |

* cited by examiner

*Primary Examiner* — Vi X Nguyen
(74) *Attorney, Agent, or Firm* — Vorys, Sater, Seymour and Pease LLP

(57) ABSTRACT

A surgical tool harvests power from a robotic surgical system having one or more robotic manipulators when a housing of the surgical tool is installed within a carriage of one of the robotic manipulators. The surgical tool harvests power via inductive coupling between an inductor of the surgical tool and a corresponding inductor of the carriage. The surgical tool may include an indicator that provides a user with an indication of remaining life of the surgical tool. The indicator may be an LED indicator that is illuminated with power generated via the inductive coupling. The indicator may also be an electro-chromic indicator that changes color when exposed to power generated via the inductive coupling. The indicator may also be a photo-chromic indicator that changes color when exposed to light from a light source powered via the inductive coupling.

18 Claims, 14 Drawing Sheets

INDUCTIVELY POWERED END OF LIFE INDICATORS FOR ROBOTIC SURGICAL INSTRUMENTS

BACKGROUND

Minimally invasive surgical (MIS) instruments are often preferred over traditional open surgical devices due to reduced post-operative recovery time and minimal scarring. During MIS procedures, a variety of instruments and surgical tools may be introduced into the abdominal cavity to engage and/or treat tissue in a number of ways to achieve a diagnostic or therapeutic effect. Various robotic systems have recently been developed to assist in MIS procedures by controlling such MIS instruments. A user (e.g., a surgeon) is able to remotely operate an MIS instrument's end effector by grasping and manipulating in space one or more controllers of the robotic system that communicate with a tool driver coupled to the surgical instrument. User inputs are processed by a computer system incorporated into the robotic surgical system and the tool driver responds by actuating the cable driven motion system and, more particularly, the drive cables. Moving the drive cables articulates the end effector to desired positions and configurations.

MIS instruments have limited life spans. For example, some MIS instruments are designed to expire after a predetermined number of uses or after a set period of time. In some cases, MIS instruments may include an indicator that provides indication when the useful life of the MIS instruments has been exhausted. Conventional instrument indicators are mechanically powered by one of the MIS instrument's tool drivers, which necessarily decreases overall functionality of the MIS instrument as such tool driver could instead be utilized for other tool functions. Moreover, conventional instrument indicators are not easily recognized and, consequently, sterilization workers often do not notice expired MIS instruments and are accidentally cleaned, sterilized, stored, and later sent to the operating room, despite having no useful operational life remaining. Once discovered in the operating room, personnel will be required to discard the MIS instrument and obtain a replacement. This results in frustration, procedural delay, and possible additional sedation time for the patient. Thus, it may be beneficial to provide indicators that do not utilize tool drivers and indicators that are more easily recognized.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to robotic surgical systems and, more particularly, to a surgical tool that harvests power during robotic surgery. The present disclosure is also related to a tool life indicator for a surgical tool used in robotic surgery.

Embodiments discussed herein describe a surgical tool that may harvest power from a robotic manipulator, wirelessly through a sterile barrier that separates the surgical tool and the robotic manipulator, via inductive coupling. The surgical tool may also include an indicator that provides a user with an indication as to the remaining useful life of the surgical tool. The indicator may be operated with power induced when the surgical tool is installed in the robotic manipulator. In some examples, the indicator is an LED indicator that is illuminated with power induced during a final operation of the surgical tool; whereas in other examples, the LED indicator is illuminated with power induced during the final operation and one or more preceding operations of the surgical tool. In some examples, the LED indicator illuminates during the final operation, whereas, in other examples, the LED indicator illuminates after the surgical tool has been removed from the robotic manipulator following the final operation. In some examples, the indicator is an electro-chromic indicator that changes color when exposed to power induced during the final operation of the surgical tool. In some examples, the indicator is a photo-chromic indicator that changes color when exposed to light emitted during the final operation of the surgical tool.

Figure 1:
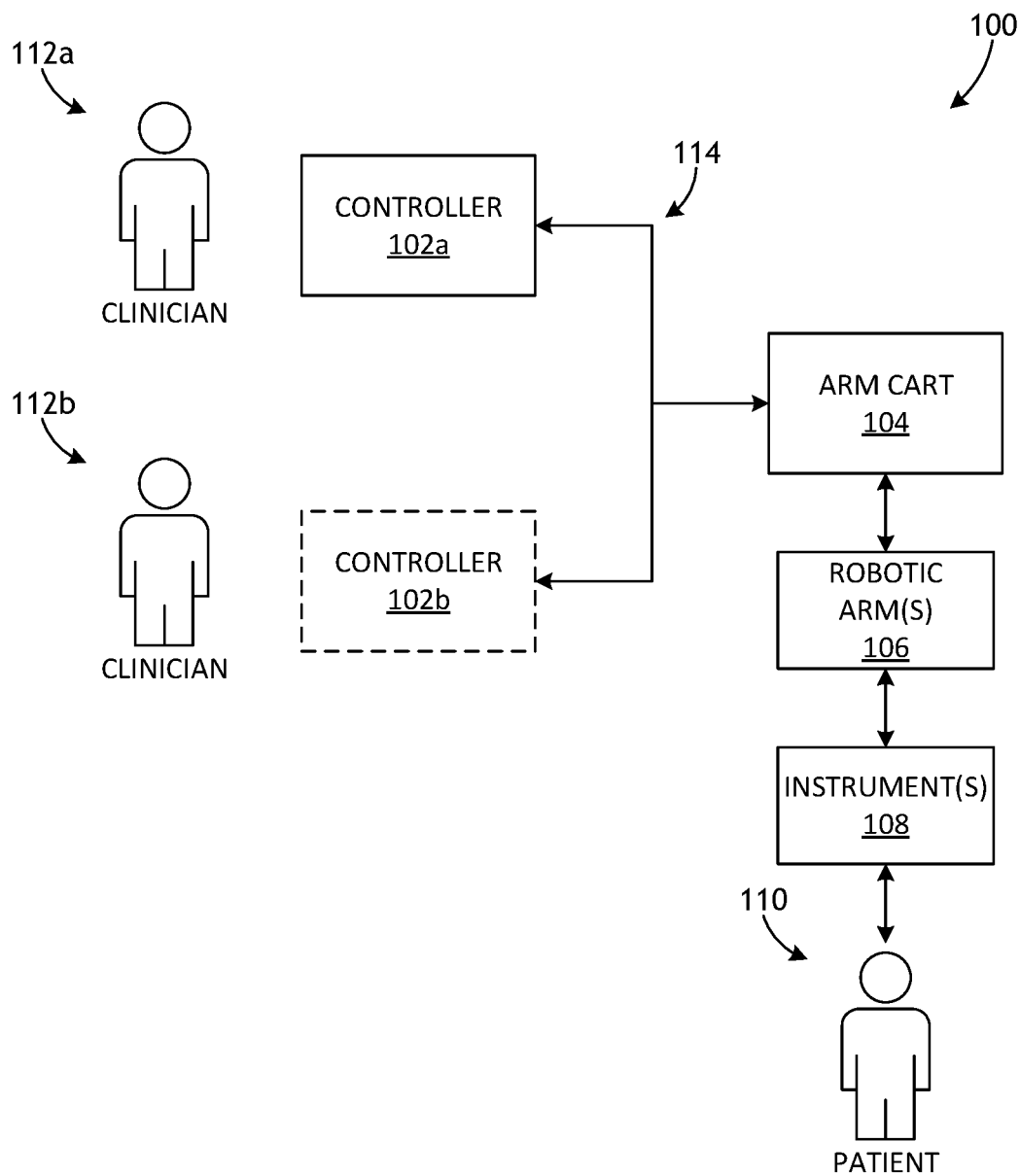
FIG. 1 is a block diagram of an example robotic surgical system that may incorporate some or all of the principles of the present disclosure.

FIGS. 1-5 illustrate the structure and operation of example robotic surgical systems and components thereof. FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to one or more robotic arms 106, alternately referred to as "tool drivers". Each robotic arm 106 may include and otherwise mount one or more surgical tools or instruments 108 for performing various surgical tasks on a patient 110. Operation of the arm cart 104, including the arms 106 and instruments 108 may be directed by a clinician 112a (e.g., a surgeon) from the master controller 102a.

In some embodiments, a second master controller 102b (shown in dashed lines) operated by a second clinician 112b may also direct operation of the arm cart 104 in conjunction with the first clinician 112a. In such embodiments, for example, each clinician 112a,b may control different arms 106 of the arm cart 104 or, in some cases, complete control of the arm cart 104 may be passed between the clinicians 112a,b. In some embodiments, additional arm carts (not shown) may be utilized on the patient 110, and these additional arm carts may be controlled by one or more of the master controllers 102a,b.

The arm cart(s) 104 and the master controllers 102a,b may be in communication with one another via a communications link 114, which may be any type of wired or wireless communications link configured to carry suitable types of signals (e.g., electrical, optical, infrared, etc.) according to any communications protocol. The communications link 114 may be an actual physical link or it may be a logical link that uses one or more actual physical links. When the link is a logical link, the type of physical link may be a data link, uplink, downlink, fiber optic link, point-to-point link, for example, as is well known in the computer networking art to refer to the communications facilities that connect nodes of a network. Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand various embodiments and forms of the various embodiments of robotic surgery apparatus, systems, and methods disclosed herein.

Figure 2:
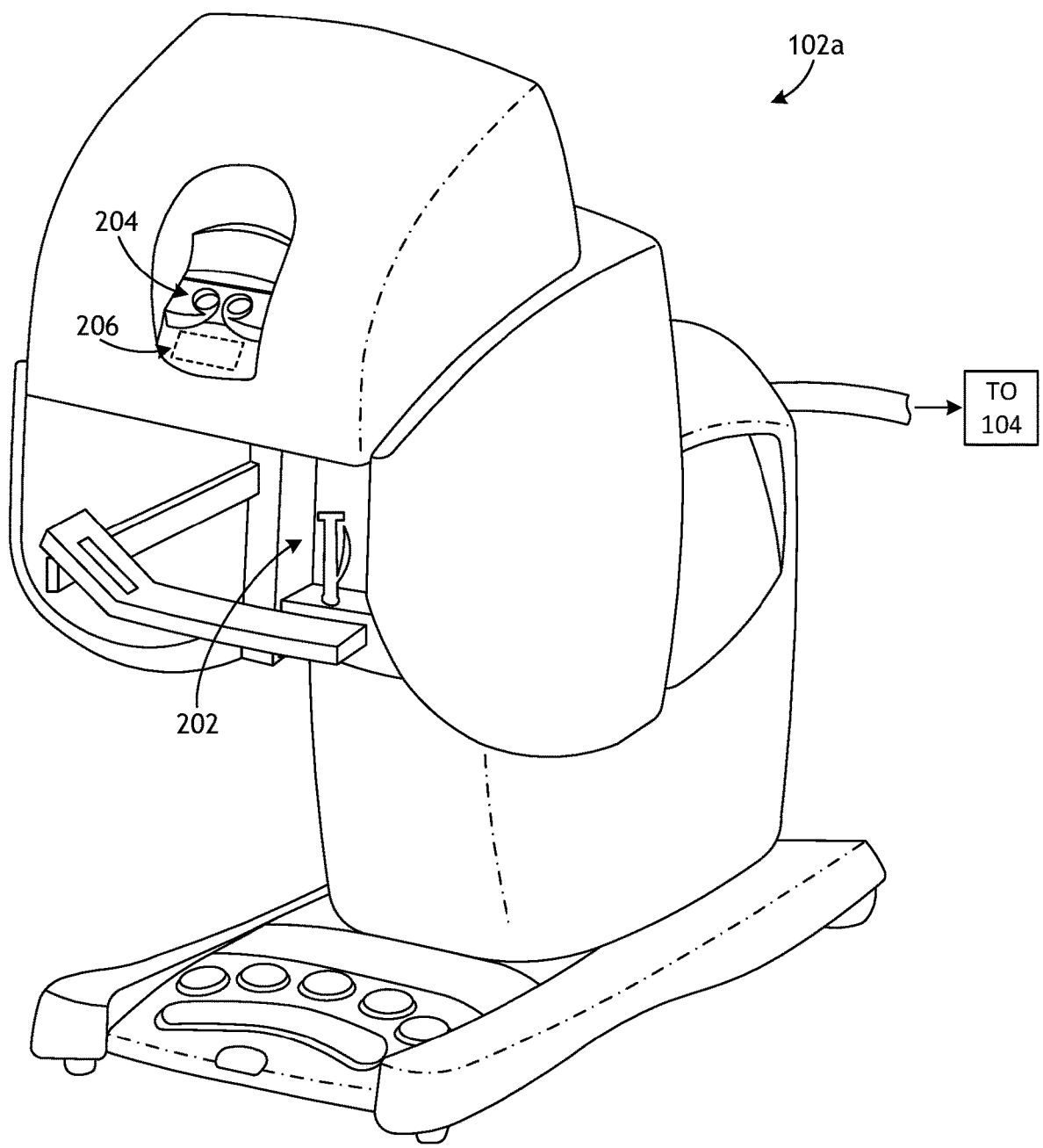
FIG. 2 is an example embodiment of the master controller of FIG. 1 that may be used to operate a robotic arm slave cart.

FIG. 2 is an example embodiment of the master controller 102a that may be used to operate a robotic arm slave cart, such as the arm cart 104 of FIG. 1. The master controller 102a and its associated arm cart 104, as well as their respective components and control systems, are collectively referred to herein as a "robotic surgical system." Examples of such systems and devices are disclosed in U.S. Pat. No. 7,524,320 and, therefore, will not be described in detail herein beyond that which may be necessary to understand various embodiments and forms of the present invention.

The master controller 102a generally includes one or more controllers 202 that can be grasped by a surgeon (e.g., the clinician 112a of FIG. 1) and manipulated in space while the surgeon views the procedure via a stereo display 204. The master controllers 202 generally comprise manual input devices designed to move in multiple degrees of freedom, and which often further have an actuatable handle for actuating a surgical instrument (e.g., the surgical instrument(s) 108 of FIG. 1), for example, for opening and closing opposing jaws, applying an electrical potential (current) to an electrode, or the like.

In the illustrated example, the master controller 102a further includes an optional feedback meter 206 viewable by the surgeon via the display 204 to provide the surgeon with a visual indication of the amount of force being applied to the surgical instrument (i.e., a cutting instrument or dynamic clamping member). Other sensor arrangements may be employed to provide the master controller 102a with an indication of other surgical instrument metrics, such as whether a staple cartridge has been loaded into an end effector or whether an anvil has been moved to a closed position prior to firing, for example.

Figure 3:
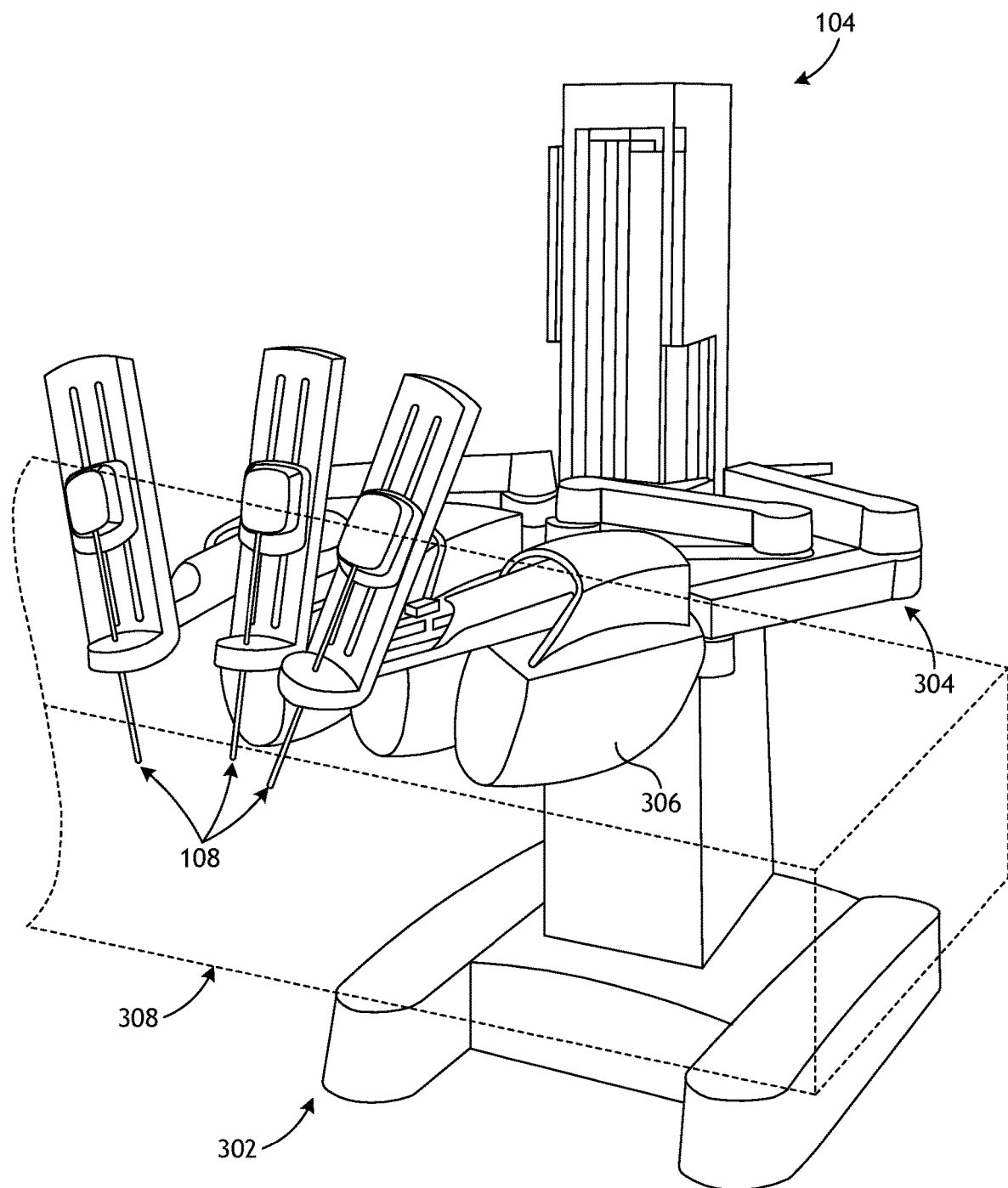
FIG. 3 depicts an example embodiment of the robotic arm cart of FIG. 1 used to actuate a plurality of surgical instruments.

FIG. 3 depicts an example embodiment of the robotic arm cart 104 used to actuate a plurality of surgical instruments 108, alternately referred to as "surgical tools." Various robotic surgery systems and methods employing master controller and robotic arm cart arrangements are described in U.S. Pat. No. 6,132,368, the contents of which are hereby incorporated by reference. As illustrated, the robotic arm cart 104 may include a base 302 that supports three surgical instruments 108, and the surgical instruments 108 are each supported by a series of manually articulable linkages, generally referred to as set-up joints 304, and a robotic manipulator 306. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 104.

The cart 104 will generally have dimensions suitable for transporting the cart 104 between operating rooms. The cart 104 may be configured to fit through standard operating room doors and onto standard hospital elevators. In some embodiments, the cart 104 may include a wheel system (or other transportation system) that allows the cart 104 to be positioned adjacent to an operating table by a single attendant. In various embodiments, an automated reloading system including a base portion may be strategically located within a work envelope 308 of the robotic arm cart 104.

Figure 4:
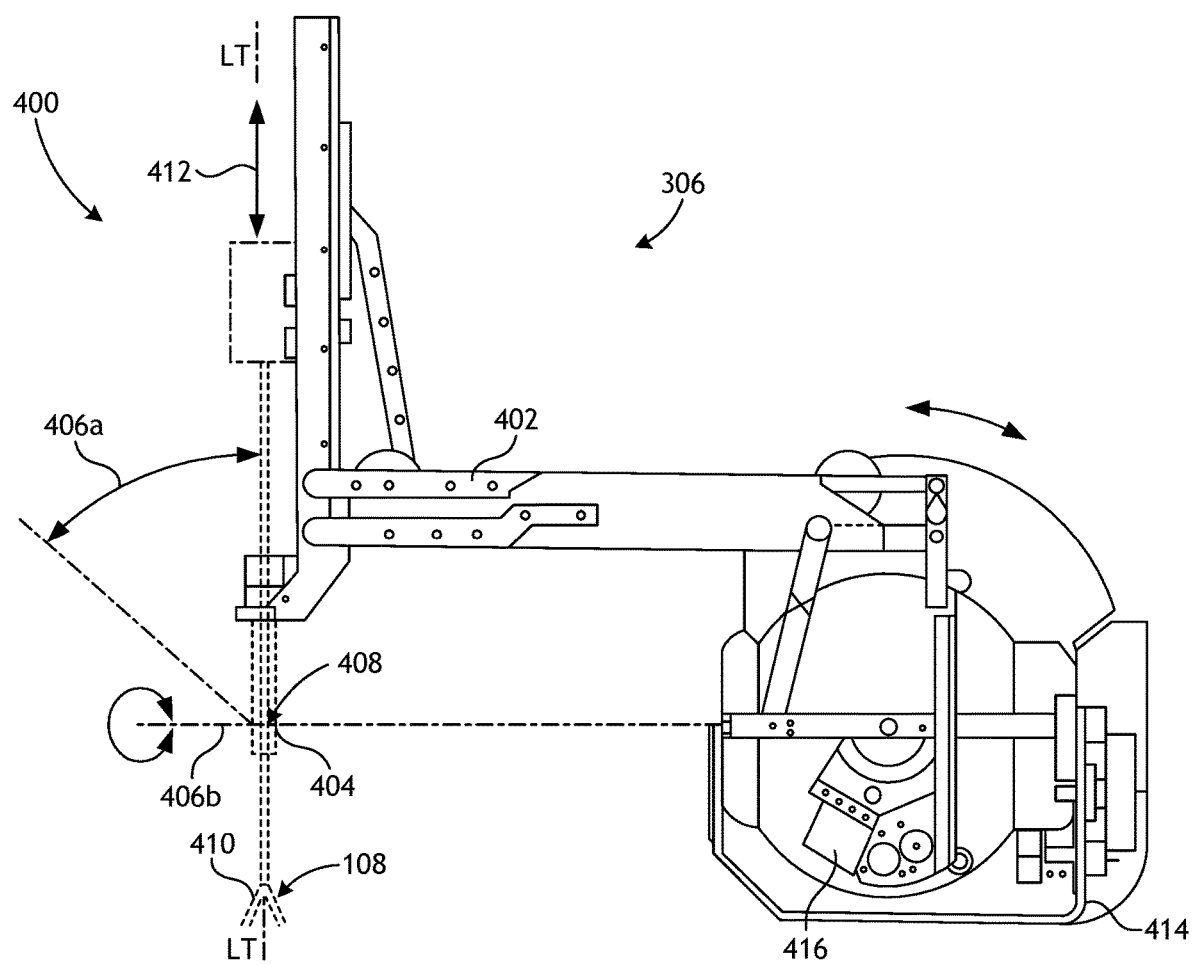
FIG. 4 is a side view schematic diagram of an example embodiment of the robotic manipulator of FIG. 3.

FIG. 4 is a side view schematic diagram of an example embodiment of the robotic manipulator 306. The robotic manipulator 306 includes a carriage 400 to which the surgical instrument 108 is attached. The carriage 400 may include one or more outputs or drivers (not illustrated) configured to transfer mechanical power to the surgical instrument 108. For example, the carriage 400 may include mechanical drivers that mechanically couple to corresponding mechanical inputs of the surgical tool 108, thereby transferring mechanical power from the robotic manipulator 306 to the surgical tool 108. Mechanical power may be utilized for various functions, including articulating and manipulating the end-effector of the surgical tool 108. The carriage 400 may also include one or more electrical connections that electronically connect to corresponding electrical inputs on the surgical tool 108 and transmit electrical power to the surgical tool 108. Electrical power may be utilized to power circuitry or other components of the surgical tool 108 (e.g., to power an indicator, charge a battery, etc.). In addition to or in lieu of the foregoing, the carriage 400 may include other energy sources that emit and direct energy on one or more portions of the surgical tool 108, such as a light source, or a heat source, etc. As described below, these other energy sources may be utilized to activate or power one or more features of the surgical tool 108. For example, in at least one embodiment, the carriage 400 may include an ultra-violet light source configured to emit light and expose a tool life indicator of the surgical tool 108 with ultra-violet light, as described below.

In at least some embodiments, the robotic surgical system 100 wirelessly supplies power to the surgical tool 108 through the sterile barrier via inductive power transfer or capacitive power transfer. For example, the carriage 400 may include a first conductor that couples to a corresponding second conductor of the surgical tool 108, such that a changing magnetic field induced in the first conductor (caused by a change in current there through) induces an electromotive force (e.g., voltage or EMF) in the second conductor. This coupling may be utilized for a variety of functions, including near field communication ("NFC") between the surgical tool 108 and the robotic manipulator 306, which allows the robotic surgical system 100 to identify and authenticate the surgical tool 108 or otherwise associate the surgical tool 108 with data stored elsewhere in the robotic surgical system 100. For example, the surgical tool 108 may include a radio-frequency identification ("RFID") tag (or other NFC enabled element) containing electronically stored information that is read by the robotic surgical system 100 when positioned proximate to the robotic manipulator 306.

As illustrated, the robotic manipulator 306 may include linkage 402 that constrains movement of the surgical instrument 108 coupled thereto. The linkage 402 includes rigid links coupled by rotational joints in a parallelogram arrangement so that the surgical instrument 108 rotates around a point 404 in space. The parallelogram arrangement constrains rotation to pivoting about a "pitch axis" that extends axis through the point 404, as indicated by a pitch arrow 406a. The links supporting the parallelogram linkage 402 are pivotally mounted to set-up joints 304 (FIG. 3) so that the surgical instrument 108 further rotates about a second axis 406b, referred to as the "yaw axis." The pitch axis and the yaw axis 406b intersect at a remote center 408, which is aligned along a shaft 410 of the surgical instrument 108.

The surgical instrument 108 may have further degrees of driven freedom as supported by the robotic manipulator 306, including sliding motion of the surgical instrument 108 along a longitudinal tool axis "LT-LT". As the surgical instrument 108 slides (translates) along the longitudinal tool axis LT-LT relative to the robotic manipulator 306 (arrow 412), the remote center 408 remains fixed relative to a base 414 of the robotic manipulator 306. Hence, the entire robotic manipulator 306 is generally moved to re-position the remote center 408.

The linkage 402 of the robotic manipulator 306 is driven by a series of motors 416. These motors 416 actively move the linkage 402 in response to commands from a processor of a control system. The motors 416 may also be employed to manipulate the surgical instrument 108.

Figure 5:
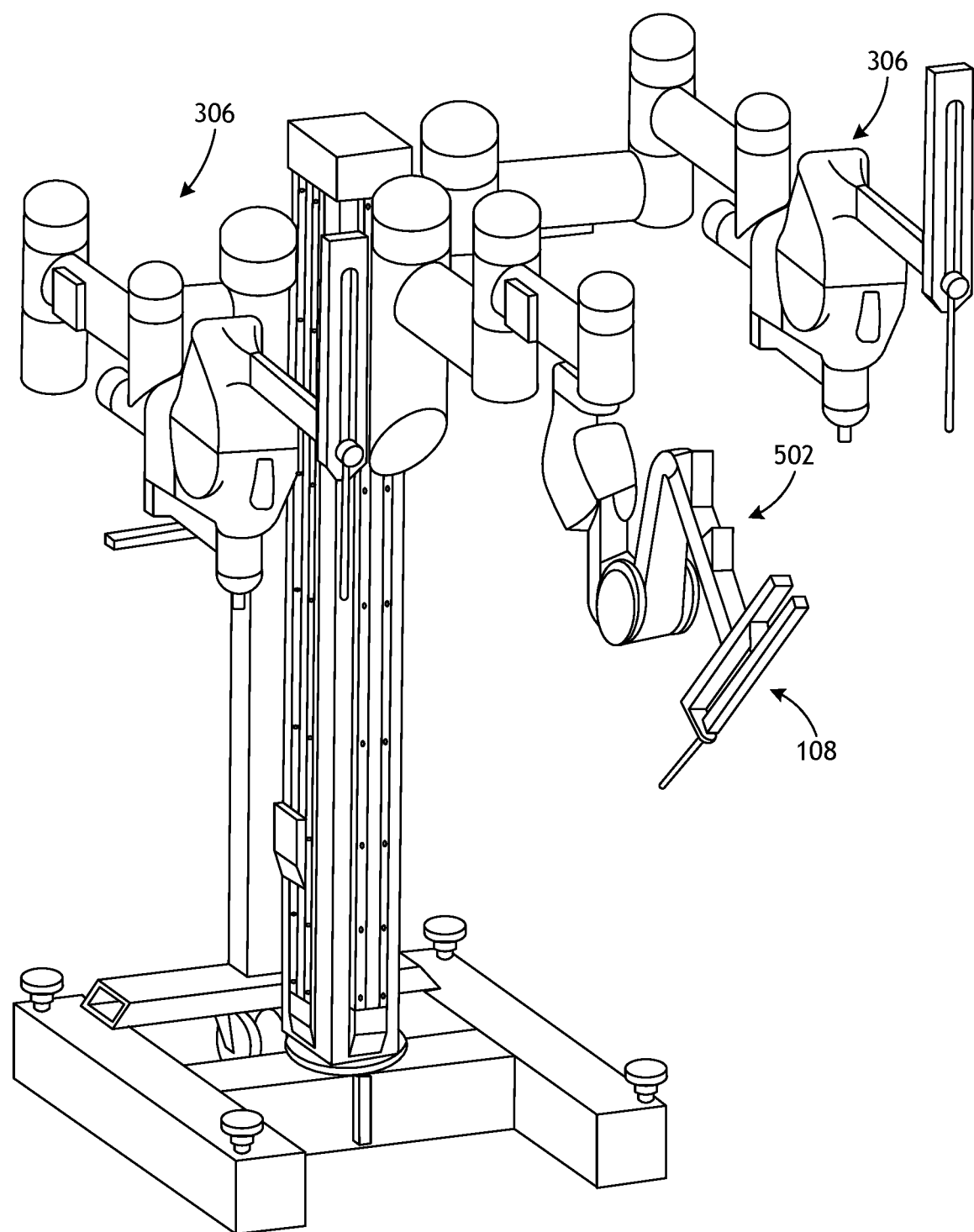
FIG. 5 is a perspective view of an alternative example robotic manipulator.

FIG. 5 is a perspective view of an alternative example robotic manipulator 502, used in conjunction with two robotic manipulators similar to the robotic manipulators 306 described in FIG. 4. As illustrated, a surgical instrument 108 is supported by the robotic manipulator 502 between the two robotic manipulators 306 generally described above. Those of ordinary skill in the art will appreciate that various embodiments of the present invention may incorporate a wide variety of alternative robotic structures, including those described in U.S. Pat. No. 5,878,193, the contents of which are hereby incorporated by reference. Additionally, while the data communication between a robotic component and the processor of the robotic surgical system 100 is primarily described herein with reference to communication between the surgical instrument 108 and the master controller 102a (FIG. 2), it should be understood that similar communication may take place between circuitry of a robotic manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 6:
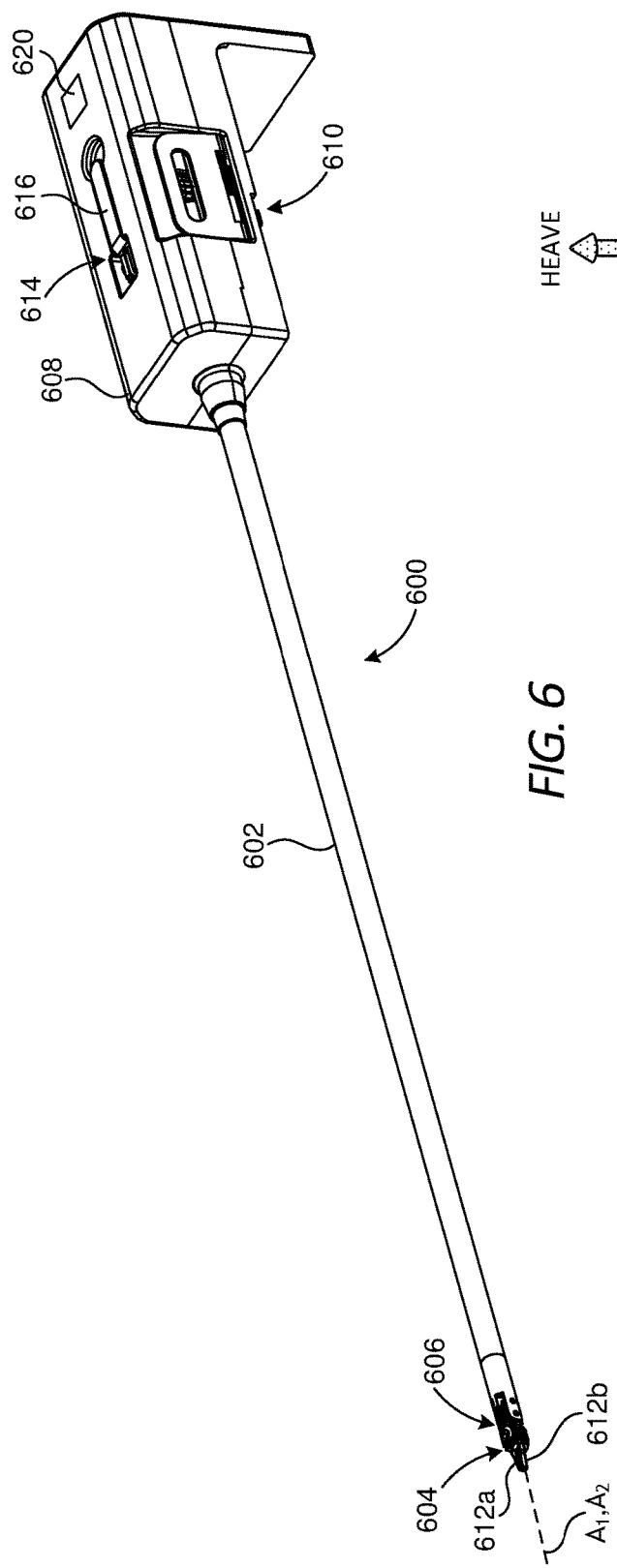
FIG. 6 is a side view of an example surgical tool that may incorporate some or all of the principles of the present disclosure.

FIG. 6 is side view of an example surgical tool 600 that may incorporate some or all of the principles of the present disclosure. The surgical tool 600 may be the same as or similar to the surgical instrument(s) 108 of FIGS. 1 and 3-5 and, therefore, may be used in conjunction with a robotic surgical system, such as the robotic surgical system 100 of FIG. 1. Accordingly, the surgical tool 600 may be designed to be releasably coupled to a tool driver included in the robotic surgical system 100. Also, the surgical tool 600 may include various electronics for actuating the surgical tool 600 as directed and for other functions. In some examples, unique identification codes for each tool are stored in the electronics of the surgical tools 600, which the robotic surgical system 100 may utilize to identify the type of tool and/or the specific tool utilized in a particular operation. In addition, the electronics of the surgical tool 600 may store the useful life of the surgical tool 600 (e.g., the use count), and the useful life of the surgical tool 600 may be determined by logic stored on one or more components of the robotic surgical system 100. Moreover, the surgical system 100 may store information related to a particular surgical tool 600, and then access and utilize that stored information when it recognizes that the particular surgical tool 600 is being utilized. For example, the robotic surgical system 100 may recognize that a particular surgical tool 600 has been installed in the robotic manipulator and then access its remaining useful life that was previously calculated, so that such useful tool life may be updated as needed following the particular operation in which the surgical tool 600 is being utilized.

As illustrated, the surgical tool 600 includes an elongate shaft 602, an end effector 604, a wrist 606 (alternately referred to as a "wrist joint") that couples the end effector 604 to the distal end of the shaft 602, and a drive housing 608 coupled to the proximal end of the shaft 602. In applications where the surgical tool is used in conjunction with a robotic surgical system (e.g., the robotic surgical system 100 of FIG. 1), the drive housing 608 can include coupling features that releasably couple the surgical tool 600 to the robotic surgical system. In the illustrated embodiment, the housing 608 includes a tool mounting portion 610 at which the surgical tool 600 is attached to a corresponding carriage of the robotic manipulator (e.g., the carriage 400 of the robotic manipulator 306 illustrated in FIG. 4) via the coupling features.

The terms "proximal" and "distal" are defined herein relative to a robotic surgical system having an interface configured to mechanically and electrically couple the surgical tool 600 (e.g., the housing 608) to a robotic manipulator. The term "proximal" refers to the position of an element closer to the robotic manipulator and the term "distal" refers to the position of an element closer to the end effector 604 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 600, the end effector 604 is configured to move (pivot) relative to the shaft 602 at the wrist 606 to position the end effector 604 at desired orientations and locations relative to a surgical site. The housing 608 includes (contains) various mechanisms designed to control operation of various features associated with the end effector 604 (e.g., clamping, firing, rotation, articulation, energy delivery, etc.). In at least some embodiments, the shaft 602, and hence the end effector 604 coupled thereto, is configured to rotate about a longitudinal axis $A_1$ of the shaft 602. In such embodiments, at least one of the mechanisms included (housed) in the housing 608 is configured to control rotational movement of the shaft 602 about the longitudinal axis $A_1$.

The surgical tool 600 may have a variety of configurations capable of performing at least one surgical function. For example, the surgical tool 600 may include, but is not limited to, forceps, a grasper, a needle driver, scissors, an electro cautery tool, a stapler, a clip applier, a suction tool, an irrigation tool, an imaging device (e.g., an endoscope or ultrasonic probe), or any combination thereof. In some embodiments, the surgical tool 600 may be configured to apply energy to tissue, such as radiofrequency (RF) energy.

The shaft 602 is an elongate member extending distally from the housing 608 and has at least one lumen extending therethrough along its axial length. In some embodiments, the shaft 602 may be fixed to the housing 608, but could alternatively be rotatably mounted to the housing 608 to allow the shaft 602 to rotate about the longitudinal axis $A_1$. In yet other embodiments, the shaft 602 may be releasably coupled to the housing 608, which may allow a single housing 608 to be adaptable to various shafts having different end effectors.

The end effector 604 can have a variety of sizes, shapes, and configurations. In the illustrated embodiment, the end effector 604 includes opposing jaws 612a, 612b configured to move (articulate) between open and closed positions. Accordingly, the end effector 604 can comprise, but is not limited to, a tissue grasper, a clip applier, scissors, a needle driver, a babcock including a pair of opposed grasping jaws, or any other surgical tool that incorporates opposing jaws. One or both of the jaws 612a, 612b may be configured to pivot at the wrist 606 to articulate the end effector 604 between the open and closed positions.

Figure 7:
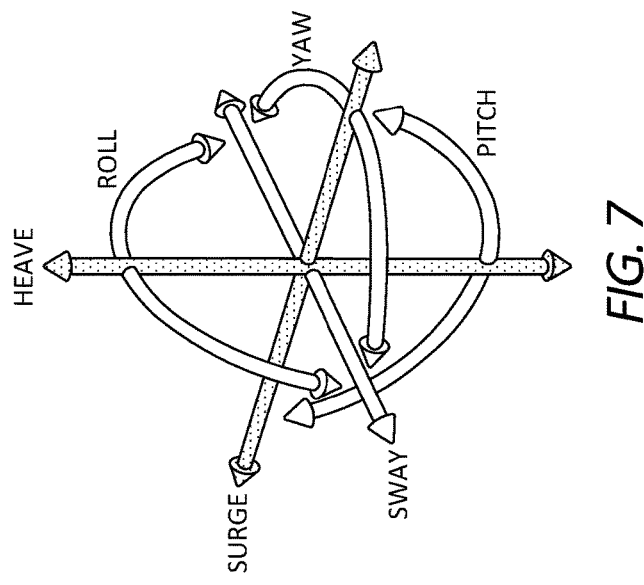
FIG. 7 illustrates potential degrees of freedom in which the wrist of FIG. 6 may be able to articulate (pivot).

FIG. 7 illustrates the potential degrees of freedom in which the wrist 606 may be able to articulate (pivot). The wrist 606 can have any of a variety of configurations. In general, the wrist 606 comprises a joint configured to allow pivoting movement of the end effector 604 relative to the shaft 602. The degrees of freedom of the wrist 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 606 (e.g., X-axis), yaw movement about a second axis of the wrist 606 (e.g., Y-axis), and combinations thereof to allow for 360° rotational movement of the end effector 604 about the wrist 606. In other applications, the pivoting motion can be limited to movement in a single plane, e.g., only pitch movement about the first axis of the wrist 606 or only yaw movement about the second axis of the wrist 606, such that the end effector 604 moves only in a single plane.

Referring again to FIG. 6, the surgical tool 600 includes a plurality of drive cables (obscured in FIG. 6) that form part of a cable driven motion system configured to facilitate movement of (articulate) the end effector 604 relative to the shaft 602. Moving the drive cables moves the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. Due to factors such as manufacturing tolerance and precision of measurement devices, the end effector 604 may not be at a precise zero angle relative to the shaft 602 in the unarticulated position, but nevertheless be considered "substantially aligned" thereto. In the articulated position, the longitudinal axes $A_1$, $A_2$ would be angularly offset from each other such that the end effector 604 is at a non-zero angle relative to the shaft 602.

The surgical tool 600 may further include a manual release assembly 614 that may be manually actuated to override the cable driven system and thereby manually articulate the end effector 604. For the illustrated embodiment, employing the manual release assembly 614 would result in the jaws 612a, 612b opening, which might prove beneficial when cleaning and/or sterilizing the surgical tool 600, or in the event of an electrical disruption or outage that renders the surgical tool 600 inoperable. Here, the manual release assembly 614 includes a release lever 616 that a user may manually grasp and lift, from a stowed position as shown, to an actuated position. When the release lever 616 is in the stowed position, the surgical tool 600 is able to operate as normal. However, as the release lever 616 is lifted and moved to the actuated position, various internal component parts of the manual release assembly 614 housed within the drive housing 608 are simultaneously moved, which result in manual articulation of the end effector 604.

According to embodiments of the present disclosure, the surgical tool 600 may further include a tool end of life indicator 620 that may be automatically activated (triggered) to provide a visual indication that the useful life of the surgical tool 600 has been exhausted and/or that the surgical tool 600 is expired. In some embodiments, the tool end of life indicator 620 may provide a visual indication that the surgical tool 600 has a certain amount of life (or uses or hours of use) remaining. Upon activation of the tool end of life indicator 620, the user will be visually notified that the service life of the surgical tool 600 has been exhausted and should not be cleaned for re-use but instead decommissioned (e.g., discarded). In some examples, the surgical tool 600 includes a single tool end of life indicator 620. In other examples, the surgical tool 600 includes a plurality of tool end of life indicators 620, where a first is activated after a first use, a second is activated after a second use, and so on; and activation of all of the plurality of tool end of life indicators 620 indicates that the surgical tool 600 has reached the end of its life. The tool end of life indicator 620 is hereafter referred to as the "indicator 620."

As illustrated, the indicator 620 may be located on the drive housing 608, such as on a top surface of the drive housing 608. It will be appreciated, however, that the depicted position of the indicator 620 is just one example and should not be considered limiting to the scope of the present disclosure. Indeed, the indicator 620 may be located at any location on the surgical tool 600 that sufficiently enables a user to notice when the indicator 620 is activated. Moreover, the indicator 620 is just one example of a means to alert the user as to whether the surgical tool 600 has any useful life remaining and, therefore, should not be considered limiting to the scope of the present disclosure.

The indicator 620 may have various configurations. For example, the indicator 620 may comprise a light-emitting diode ("LED"), an activatable electro-chromic ink or film, an activatable photo-chromic ink or film, an activatable thermo-chromic ink or film, or any combination thereof. In addition, the surgical tool 600 may include two or more indicators 620 of the same or different type. Regardless of its configuration, a variety of means may be utilized to activate and/or power the indicator 620. For example, inductive coupling may be utilized to activate and/or power the indicator 620 as hereinafter described. However, while the indicator 620 is described herein with reference to inductive coupling, other means may be utilized without departing from the present disclosure. For example, the indicator 620 may be activated and/or powered via mechanical coupling elements, electrical coupling elements, magnetic coupling elements, and/or other telemetry modalities including infrared, ultra-violet, or the like.

Various metrics may be implemented to measure the useful life of the surgical tool 600. For example, the useful life may be the number of procedures that the surgical tool 600 has been utilized (e.g., twenty procedures), or it may be the number of hours that the surgical tool 600 has been utilized, the number of articulations or movements that the surgical tool 600 has made, a combination thereof, etc. As mentioned, the indicator 620 may provide indication that the surgical tool 600 has exhausted its useful life or is expired, and/or that the surgical tool 600 has a certain amount of life (or uses or hours of use) remaining.

Figure 8:
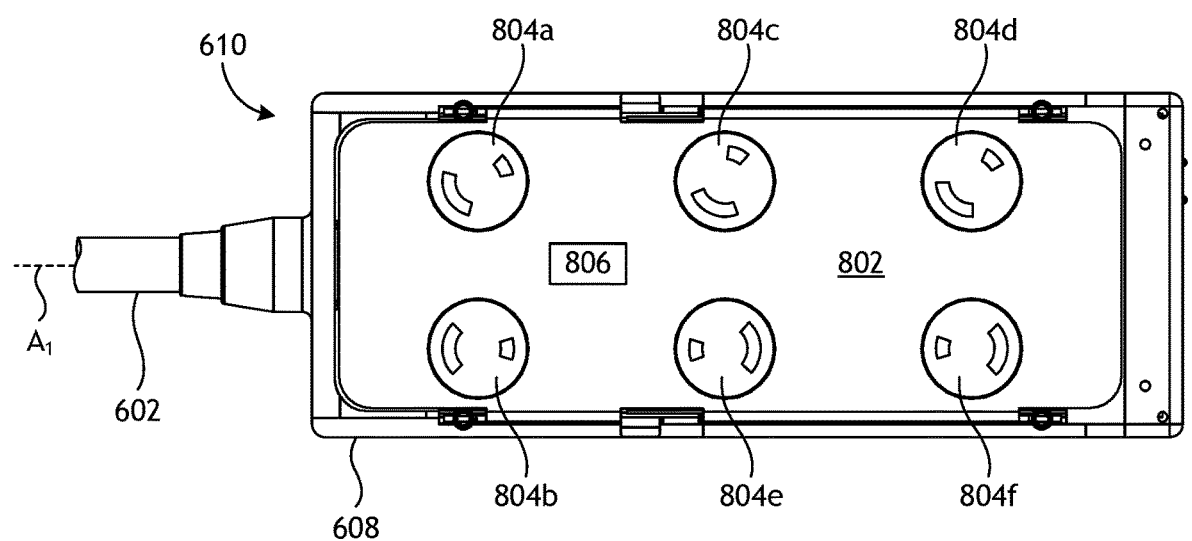
FIG. 8 is a bottom view of the drive housing illustrating the tool mounting portion of the surgical tool of FIG. 6.

FIG. 8 is a bottom view of the drive housing 608 illustrating the tool mounting portion 610 thereof, according to one or more embodiments. The tool mounting portion 610 may be used to mount the drive housing 608 of the surgical tool 600 to a robotic manipulator (e.g., the robotic manipulators 306, 502 of FIGS. 3 and 5, respectively). The tool mounting portion 610 may releasably attach (couple) the drive housing 608 to the robotic manipulator in a variety of ways, such as by clamping thereto, clipping thereto, or slidably mating therewith. In some embodiments, the tool mounting portion 610 may include an array of electrical connecting pins, which may be coupled to an electrical connection on the carriage and/or tool driver(s).

The tool mounting portion 610 includes or otherwise provides a tool interface 802 configured to operatively couple the surgical tool 600 to outputs or drivers of the robotic manipulator (e.g., in the carriage 400 of the robotic manipulator 306 of FIG. 4). The tool interface 802 thus includes one or more inputs that engage corresponding outputs or drivers of the robotic manipulator described above. In the illustrated embodiment, the tool interface 802 includes a plurality of mechanical drive inputs, shown as drive inputs 804a, 804b, 804c, 804d, 804e, and 804f. In at least one embodiment, each drive input 804a-f comprises a rotatable disc configured to align with and couple to a corresponding output actuator (not shown) of a given robotic manipulator. Here, rotation of the drive inputs 804a-f actuates the corresponding drive cables (not illustrated) to control operation of the surgical tool 600. For example, actuation of the drive inputs 804a-f may control rotation of the elongate shaft 602 about its longitudinal axis $A_1$, control a locking mechanism, articulate the end effector 604, manipulate the jaws 612a, 612b, etc. Each of the drive inputs 804a-f may be actuated based on user inputs communicated to a tool driver coupled to the tool interface 802, and the user inputs may be received via a computer system incorporated into the robotic surgical system.

As mentioned above, the surgical tool 600 may wirelessly communicate with the robotic surgical system 100. In particular, the robotic surgical system 100 may utilize NFC protocols to identify or authenticate the surgical tool 600 or to associate the surgical tool 600 with stored data related to that particular surgical tool 600. In at least some embodiments, the surgical tool 600 includes a tag that may be read remotely and wirelessly, without physical contact, when excited with energy emitted from the robotic manipulator. The tag includes an integrated circuit (or chip) that stores and processes information and modulates and demodulates signals (i.e., radio frequency or "RF" signals) and an antenna that receives and transmits the signal. The tag may include a battery and periodically self-activate to transmit a signal, or may include a battery but activate to transmit a signal when in the presence of the robotic manipulator (or other reader device), or may not include a battery and activate to send a signal when excited by the robotic manipulator (or other reader device). The tag may be read-only, having information assigned thereon, or may be read/write, where information may be written into the tag one or more times. In these examples, the robotic manipulator (or reader device) transmits an encoded radio signal to interrogate the tag within the surgical tool 600. The tag receives the encoded radio signal and responds by sending the identification and/or other information stored in the integrated circuit (e.g., serial number, use count, usage time, manufacture date, expiration date, etc.) to the robotic manipulator so that it may be analyzed by the robotic surgical system 100. The robotic surgical system 100 may differentiate between the surgical tools 600 as the tags include unique identification information.

Various technologies may be utilized to permit communication between the tag of the surgical tool 600 and the robotic manipulator (i.e., the reader or interrogator), including inductive coupling and capacitive coupling. In embodiments utilizing inductive coupling, the robotic manipulator emits a magnetic field and, when the antenna (of the tag) enters the magnetic field, the integrated circuit varies its antenna's response resulting in a perturbation of the magnetic field, which can be detected by the robotic manipulator and interpreted by the robotic surgical system 100. In embodiments utilizing capacitive coupling, the robotic manipulator emits a propagating electromagnetic wave and, when this wave impinges on the antenna (of the tag), the integrated circuit modifies its antenna radar cross section in such a way that the reflected signal containing the information on the integrated circuit may be detected by the robotic manipulator for analyzation by the robotic surgical system 100. Thus, the surgical tool 600 may include a coupling portion 806 configured to permit such communication between the tag and the robotic manipulator when positioned a sufficiently proximate to a corresponding coupling portion of the robotic manipulator (not illustrated). In these examples, the coupling portion 806 includes an inductor that couples with an inductor of the corresponding coupling portion when the surgical tool 600 is moved near the robotic manipulator. In the illustrated example, the coupling portion 806 is provided on the tool interface 802 so that the tag may wirelessly communicate with the robotic manipulator (i.e., through the sterile barrier). In addition to providing a data transfer means as described above, positioning the coupling portion 806 sufficiently proximate to the coupling portion of the robotic manipulator may permit the surgical tool 600 to harvest power from the robotic manipulator. For example, the surgical tool 600 may harvest power and use that harvested power to operate features such as the indicator 620 and/or to charge a battery or capacitor of the surgical tool 600.

In some embodiments, the indicator 620 of the surgical tool 600 is an LED light source. The LED light source may be electrically connected to circuitry of the surgical tool 600 or other on-board electronics of the surgical tool 600, and may be contained within the housing 608. In at least some embodiments, the surgical tool 600 includes an NFC integrated circuit and the LED light source is electrically connected to the NFC integrated circuit. The inductor of the coupling portion 806 is also electrically connected to (or integrated in) the NFC integrated circuit, thereby permitting the surgical tool 600 to harvest power from the robotic manipulator, wirelessly through the sterile barrier, via induction between the coupling portion 806 of the surgical tool 600 and the corresponding coupling portion of the robotic manipulator. Thus, the LED light source may be inductively powered via NFC circuitry, rather than drawing power from one or more of the (mechanical) drive inputs 804a-f, one or more electrical connections, or a battery, etc. Managing the LED light source via the NFC integrated circuit within the surgical tool 600, which inductively couples to the robotic manipulator, allows the drive inputs 804a-f to be utilized for other functions (e.g., manipulation of the end effector 604) and also prevents the need of a separate electronic reader or interrogator device to communicate tool life to sterilization staff. The LED light source and the coupling portion 806, together with the NFC circuit to which they are connected or integrated, may be of the type capable of withstanding autoclave temperatures and cleaning chemicals encountered during cleaning and sterilization.

FIGS. 9A-9E are circuit diagrams illustrating illumination of an LED indicator 900 via coupling of NFC circuitry, according to various embodiments of the disclosure. As illustrated in these circuit diagrams, the NFC circuitry includes a robot side circuit 902 having a robot inductor coil 904 integrated within the robotic manipulator and a tool side circuit 906 having a tool inductor coil 908 that corresponds with the coupling portion 806 on the tool interface 802. The LED indicator 900 is connected to or integrated within the tool side circuit 906, which is physically separated from the robot side circuit 902 by a sterile barrier 910. The tool side circuit 906 also includes a capacitor C that functions as a power storage device or battery to power the LED indicator 900 and stores energy produced when the robot inductor coil 904 and the tool inductor coil 908 are inductively (or capacitively) coupled. In these embodiments, the robotic surgical system supplies voltage to the robot side circuit 902, which induces voltage in the tool side circuit 906 via inductive coupling of the robot inductor coil 904 and the tool inductor coil 908. Thus, induction across the sterile barrier 910 wirelessly generates power in the tool side circuit 906, without any physical electronic connections traversing the sterile barrier 910.

The tool side circuit 906 illuminates the LED indicator 900 depending on the remaining useful life of the surgical tool 600. For example, the tool side circuit 906 may be configured to illuminate the LED indicator 900 after a certain number of uses (e.g., twenty) of the surgical tool 600 or when the useful life of the surgical tool 600 has otherwise expired. Once the LED indicator 900 has been illuminated, a capacitor C included in the tool side circuit 906 may slowly discharge and power the LED indicator 900 for a period of time thereafter (e.g., twenty-four hours or more), and thereby provide operating room and sterilization staff with clear indication that the surgical tool 600 is exhausted and should be discarded, and not cleaned, sterilized, and stored for subsequent use. In at least one embodiment, to prolong the power output of the capacitor C, the tool side circuit 906 may be designed to make the LED indicator 900 blink intermittently.

Figure 9A:
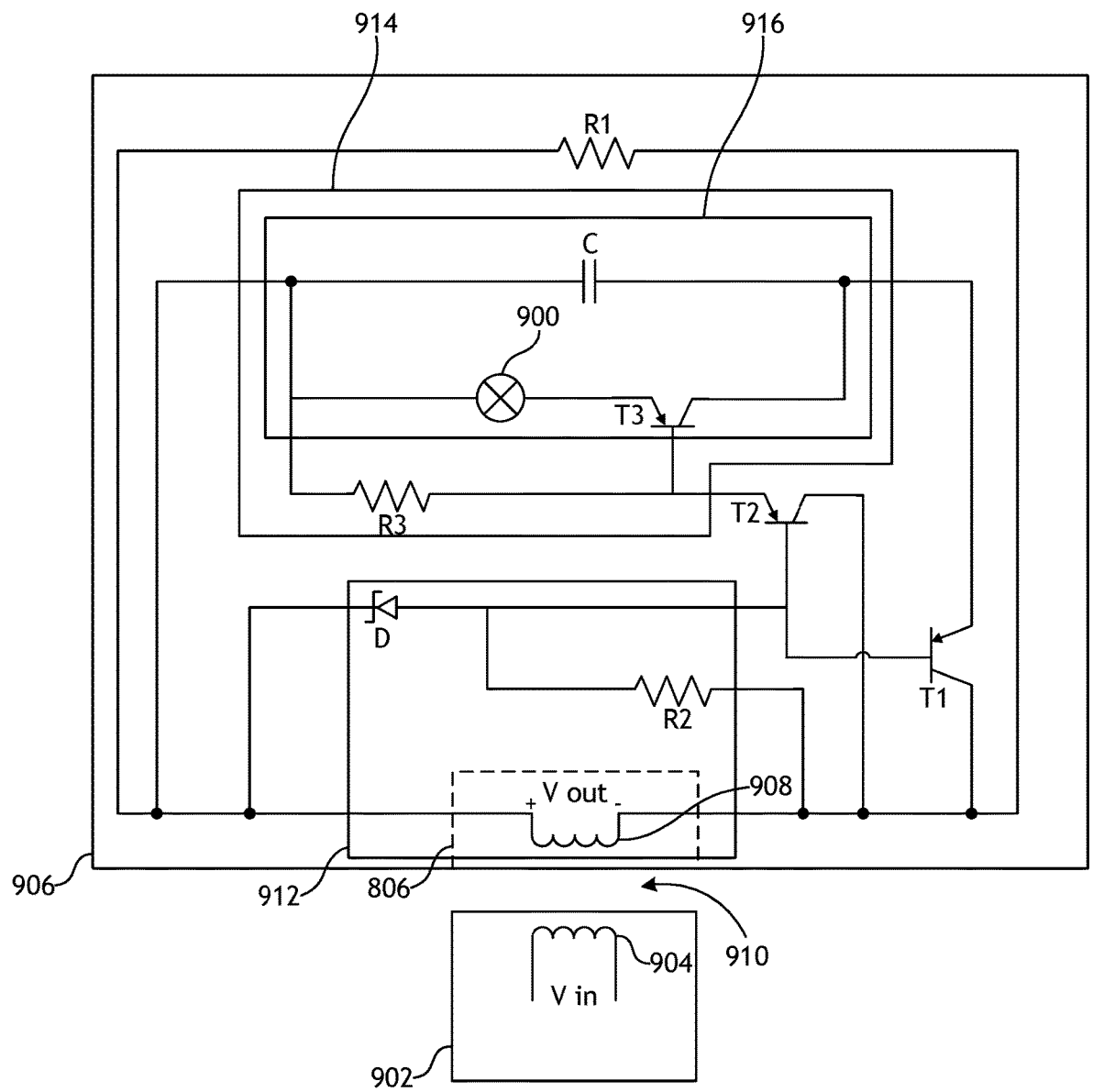
FIGS. 9A-9E are circuit diagrams of the surgical tool of FIG. 6 for inductively harvesting power from the robotic manipulator and activating an indicator, according to one or more embodiments.

With reference to FIG. 9A, an input voltage $V_{in}$ is supplied to the robot side circuit 902 via the robotic manipulator/robotic surgical system. The input voltage $V_{in}$ induces an output voltage $V_{out}$ in the tool side circuit 906 via induction between the robot inductor coil 904 and the tool inductor coil 908. In the illustrated embodiment, the tool side circuit 906 is configured to cause illumination of the LED indicator 900 immediately after the final designed use of the surgical tool 600 (e.g., after the twentieth use). To achieve this, the input voltage $V_{in}$ supplied by the robot side circuit 902 during the first use and during each subsequent use up to and including the penultimate use (e.g., the nineteenth use of a twenty use life span) is less than the input voltage $V_{in}$ induced on the final use (e.g., the twentieth use). For the surgical tool 600 designed to expire after a number (X) of uses (T), a first input voltage $V_{in}^1$ is supplied during the first use ($T^1$) and each use thereafter through the penultimate use ($T^{X-1}$), and a second input voltage $V_{in}^2$ that is greater than the first input voltage $V_{in}^1$ is supplied during the last use ($T^X$). Thus, the first input voltage $V_{in}^1$ is less than the second input voltage $V_{in}^2$ ($V_{in}^1 < V_{in}^2$), with the first input voltage $V_{in}^1$ being supplied on uses $T^1$ to $T^{X-1}$ and the second input voltage $V_{in}^2$ being supplied on use $T^X$.

The first input voltage $V_{in}^1$ may be selected such that a corresponding first output voltage $V_{out}^1$ induced thereby is below a Zener voltage of a Zener diode D, and the second input voltage $V_{in}^2$ may be selected such that a corresponding second output voltage $V_{out}^2$ induced thereby is above the Zener voltage of the Zener Diode D. When the first output voltage $V_{out}^1$ is induced, a circuit portion 912 having a resistor R2 and the transistors T1, T2 are open so that the remaining portions of the tool side circuit 906 are open and no current flows there through. When the second output voltage $V_{out}^2$ is induced, current flows into the inputs of transistors T1, T2, thereby enabling the transistors T1, T2 and completing circuits to the capacitor C and the LED indicator 900, respectively. Thus, enabling the transistor T1 with current completes the portion of the tool side circuit 906 in which the capacitor C is connected so that the output voltage $V_{out}^2$ charges the capacitor C. Also, enabling the transistor T2 completes a portion of the tool side circuit 906 to ground a resistor R3, thereby pulling current from a transistor T3 which effectively opens the portion of the tool side circuit 906 in which the LED indicator 900 is connected. Thus, the tool side circuit 906 is configured to prevent illumination of the LED indicator 900 while the second output voltage $V_{out}^2$ is being supplied and when the surgical tool 600 is attached to the robotic manipulator. Also, the tool side circuit 906 may include various features or communication functions, represented by a first resistance or resistor R1, which are powered by all levels of the output voltage $V_{out}$ (e.g., the first output voltage $V_{out}^1$ and the second output voltage $V_{out}^2$). Thus, R1 may represent various loads or circuits that would be powered by $V_{out}$.

The second output voltage $V_{out}^2$, which is larger than the first output voltage $V_{out}^1$, charges the capacitor C when the surgical tool 600 is used for the final time in the robotic manipulator. After the second output voltage $V_{out}^2$ has energized the capacitor C during the final use, the surgical tool 600 is removed from the robotic manipulator such that no more output voltage $V_{out}$ is induced in the tool side circuit 906. Thus, removing of the surgical tool 600 from the robotic manipulator causes the output voltage $V_{out}$ to drop to zero (0 V), which in turn effectively opens the transistors T1, T2 such that the only remaining completed portion of the tool side circuit 906 having current flow is a circuit portion 914 interconnecting the capacitor C, the resistor R3, the transistor T3, and the LED indicator 900. As the capacitor C dissipates into the transistor T3, the current from the capacitor C effectively closes the transistor T3, which thereby completes an LED circuit 916 and allows the capacitor C to illuminate the LED indicator 900. The resistors R2, R3 may be sized to balance current needed to activate the transistors T1, T2, T3, and manage the time release of the capacitor C such that the LED indicator 900 is illuminated for a desired amount of time.

Figure 9B:
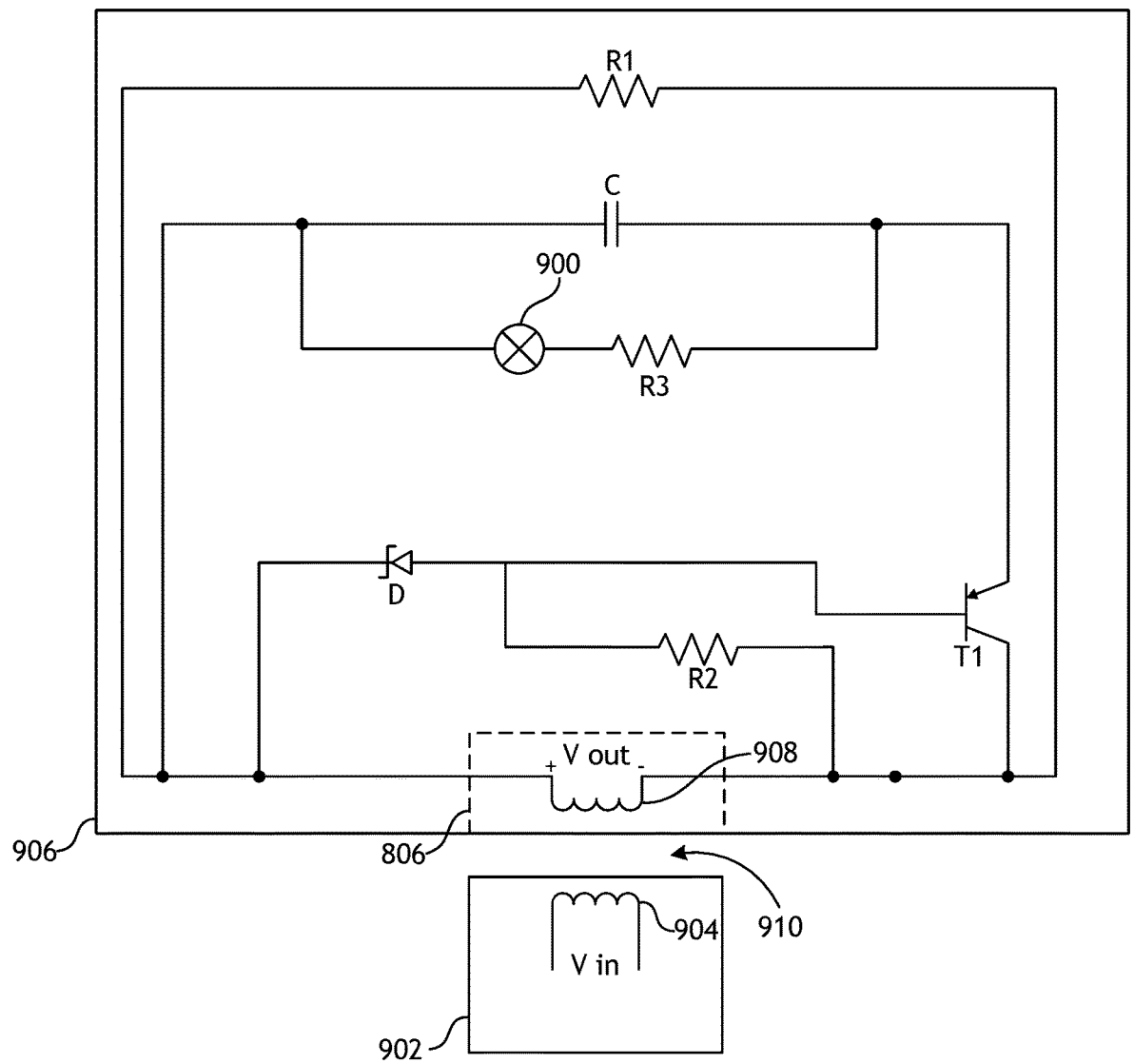

FIG. 9B illustrates a variation of the tool side circuit 906 of FIG. 9A, according to one or more embodiments. Here, the tool side circuit 906 is similar to that described with reference to FIG. 9A, except that it is configured to illuminate the LED indicator 900 during the final use $T^X$ when the output voltage $V_{out}^2$ is being induced. When the transistor T1 is enabled with current, the second output voltage $V_{out}^2$ charges the capacitor C. In this example, however, because there is no transistor(s) switching off the LED indicator 900 during the final use $T^X$ (i.e., transistors T2, T3 are absent), the LED indicator 900 is illuminated when the second output voltage $V_{out}^2$ is induced in the tool side circuit 906. Thus, FIG. 9B illustrates an example where the tool side circuit 906 permits the second output voltage $V_{out}^2$ to charge the capacitor and illuminate the LED indicator 900 simultaneously. The tool side circuit 906 of FIG. 9B may be utilized in various situations, for example, where the LED indicator 900 is obstructed (or hidden) from view when the surgical tool 600 is installed within the robotic manipulator, or where it is not a requirement that the LED indicator 900 be unlit during use.

Figure 9C:
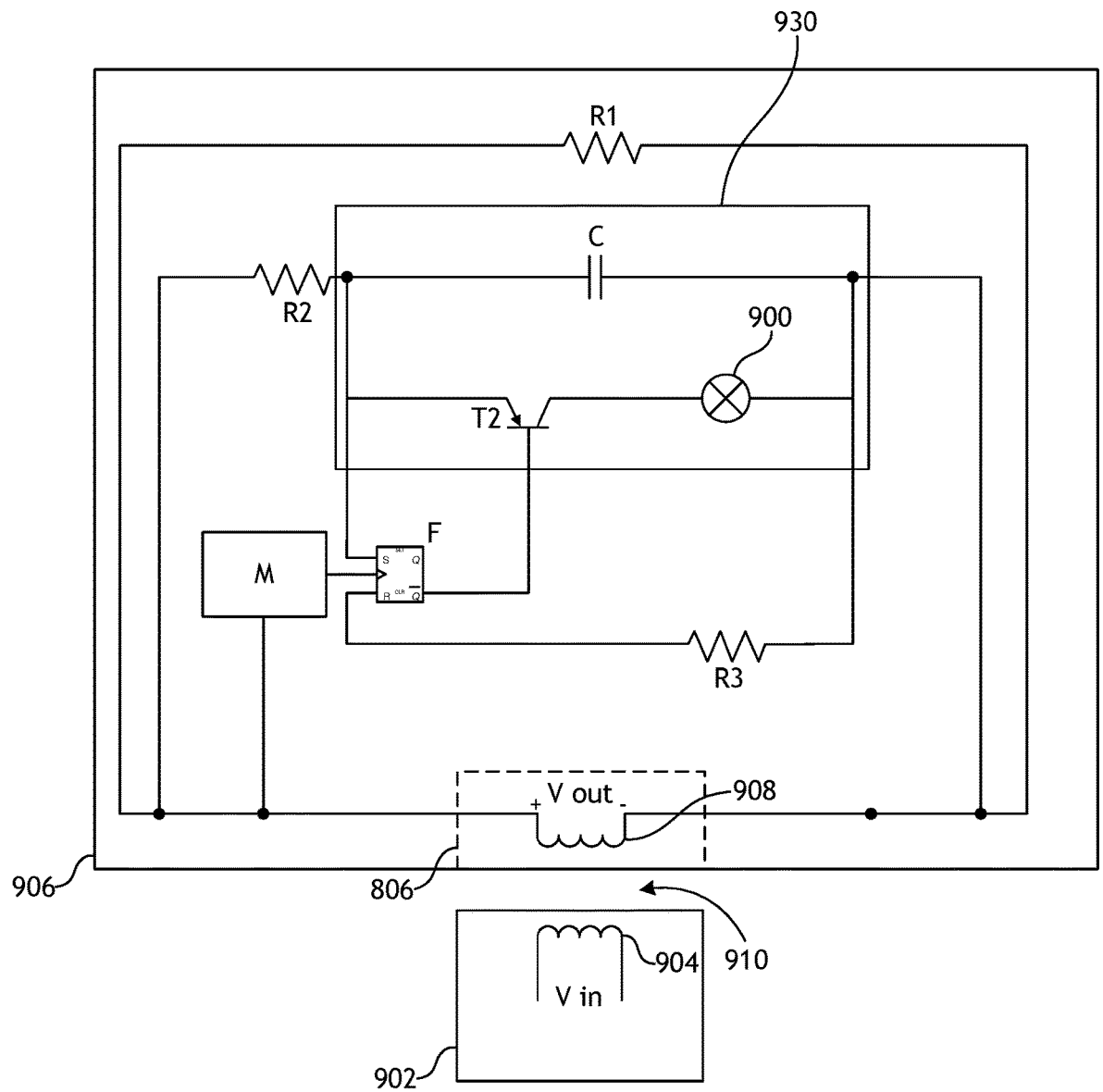

FIG. 9C illustrates an example of the tool side circuit 906 configured to charge the capacitor C over the life of the surgical tool 600, according to one or more embodiments. In this example, the capacitor C is in parallel with other functions of the tool side circuit 906 so that it is consistently charged when the output voltage $V_{out}$ is induced at any level. Thus, the capacitor C is charged when the second output voltage $V_{out}^2$ is induced and when the first output voltage $V_{out}^1$ is induced. This permits the capacitor to slowly build a charge over the life of the surgical tool 600 rather than just during a final use.

As illustrated, the tool side circuit 906 includes a microprocessor M connected to a flip-flop F. The microprocessor M accesses data, such as a designed useful life of the surgical tool 600. When the microprocessor M determines that the designed useful tool life is equal to the final use of the surgical tool 600 (e.g., when powered with the second output voltage $V_{out}^2$), the microprocessor M sends a signal to a reset of the flip-flop F. The reset then causes the flip-flop F to change the signal sent to its second port (e.g., from 0 to 1), thereby sending current to an input of the transistor T2 to effectively close the transistor T2. Powering the transistor T2 thus closes (completes) a circuit portion 930 between the LED indicator 900 and the (charged) capacitor C, thereby illuminating the LED indicator 900. The LED indicator 900 remains illuminated after removal of the surgical tool 600 from the robotic manipulator due to the energy stored in the capacitor C, which will dissipate over time.

Figure 9D:
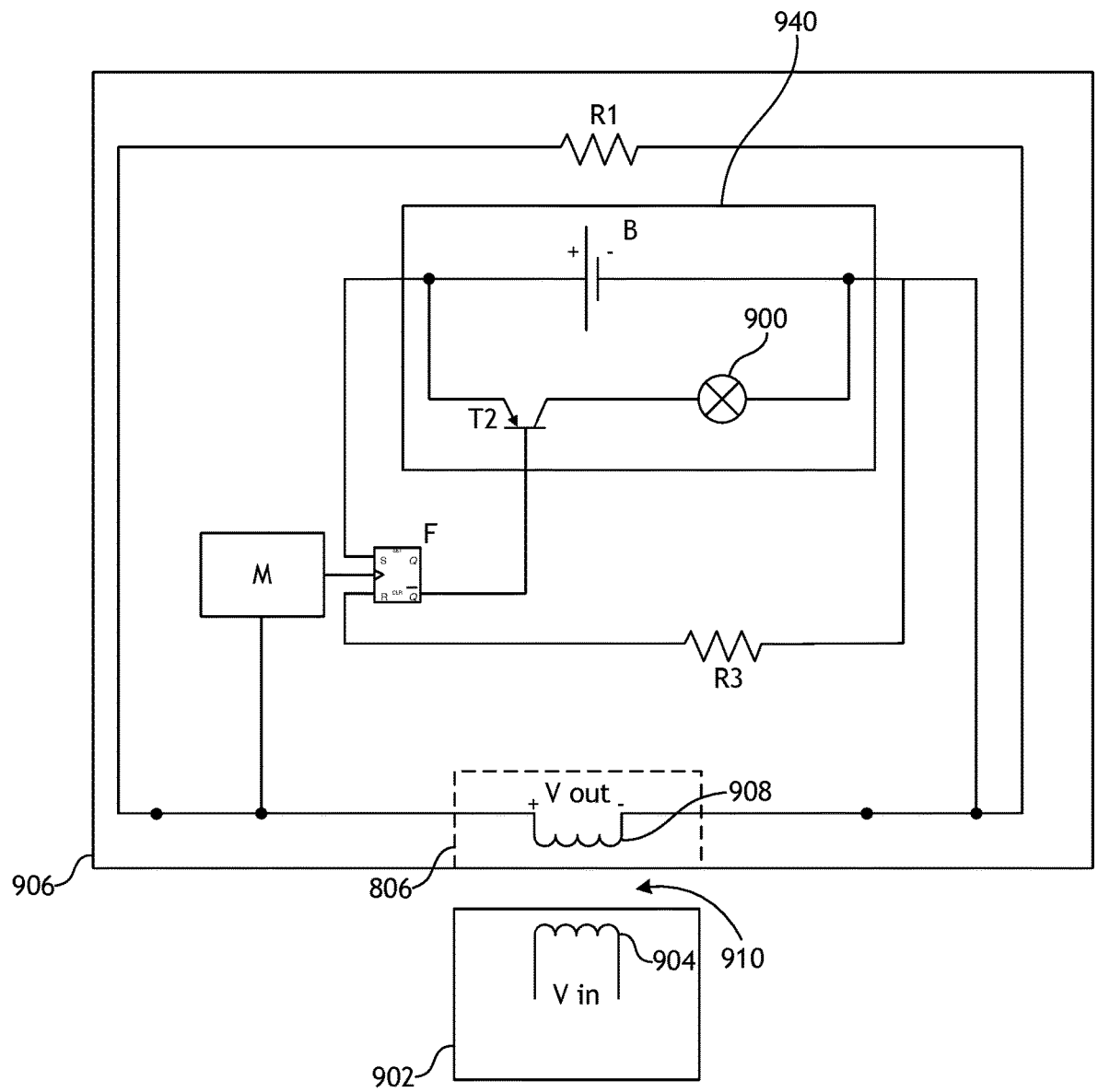

FIG. 9D illustrates an example of the tool side circuit 906 having a battery B, according to one or more embodiments. The tool side circuit 906 is similar to that described with reference to FIG. 9C, except that the tool side circuit 906 of FIG. 9D incorporates the battery B instead of the capacitor C. The microprocessor M accesses data, such as a designed useful life of the surgical tool 600. When the microprocessor M determines that the designed useful tool life is equal to the final use of the surgical tool 600 (e.g., when powered with the second output voltage $V_{out}^2$), the microprocessor M sends a signal to the reset of the flip-flop F. The reset then causes the flip-flop F to change the signal to the second port (e.g., from 0 to 1), thereby sending current to the transistor T2 and effectively closing the transistor T2. Powering the transistor T2 closes (completes) a circuit portion 940 between the LED indicator 900 and the battery B, thereby illuminating the LED indicator 900 which will remain illuminated after the surgical tool 600 has been removed from the robotic manipulator until the battery B has been drained of power. The duration that the LED indicator 900 remains illuminated after removal of the surgical tool 600 from the robotic manipulator depends on the storage capability of the battery B.

Figure 9E:
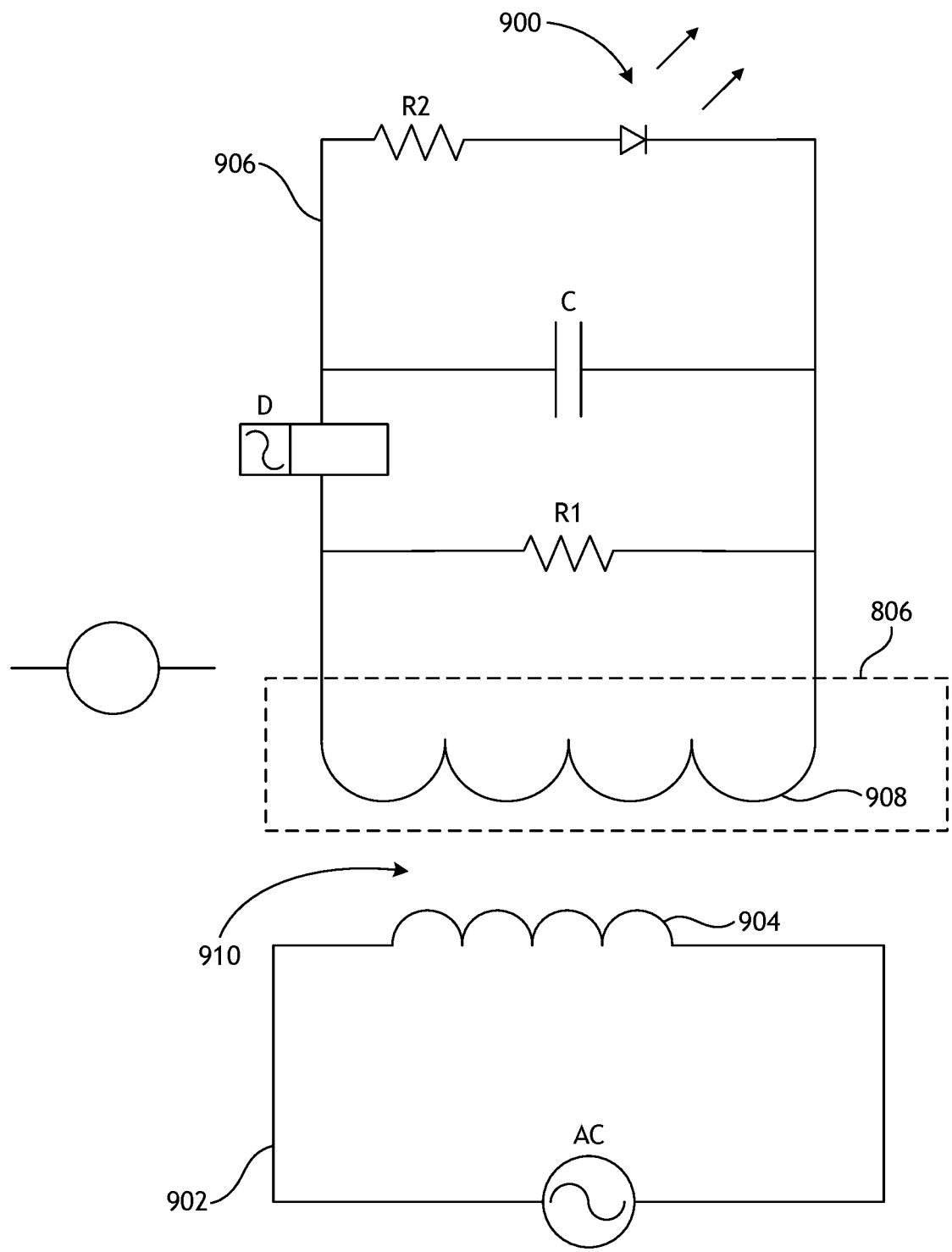

FIG. 9E illustrates another variation of the tool side circuit 906, according to one or more embodiments. In this example, the capacitor C is charged on the final use of the surgical tool 600 when the second output voltage $V_{out}^2$ is induced. Here, the LED indicator 900 is also illuminated when the second output voltage $V_{out}^2$ is induced. After the surgical tool 600 has been removed from the robotic manipulator, the capacitor C will power the LED indicator 900 using energy stored therein and the illumination output from the LED indicator 900 will slowly fade (diminish) over several hours thereafter as the capacitor C discharges.

In some embodiments, the indicator 620 of the surgical tool 600 may comprise an electro-chromic indicator that may change color in response to an applied voltage and/or current. For example, an electro-chromic ink (or material) may be applied to a film to form an electro-chromic film. The electro-chromic film may then be placed (or layered) between a backer plate and a clear protective cover, and the electro-chromic film may be visible through the protective cover. The protective cover, the electro-chromic film, and the backer plate may be laminated together to form the electro-chromic indicator. The electro-chromic indicator may then be positioned on housing 608 of the surgical tool 600 with the protective cover facing outward therefrom, as illustrated in FIG. 6. When exposed to a voltage, the electro-chromic indicator changes colors, and the change in color may be dependent upon the exposure time, voltage, and/or current. Thus, the coloring of the electro-chromic indicator may be accelerated by supplying more voltage, whereas, exposure time may be increased if additional input power is required. The electro-chromic indicator may be irreversible, such that the electro-chromic ink may not return to its original color after it has been activated to change color.

The foregoing electro-chromic indicator may be coupled with one or more features of tool housing 608 that are electrically activated during use of the surgical tool 600. In some examples, the electro-chromic ink may be provided on a flex-circuit that is electrically connected to a printed circuit board ("PCB") of the surgical tool 600, or the electro-chromic ink may be printed directly on the PCB. However, various suitable ways in which an electro-chromic ink may be incorporated into the tool housing 608 to visually indicate use of the surgical tool 600 will be apparent to those of ordinary skill in the art in view of the teachings herein. By way of example only, the electro-chromic material may comprise an electro-chromic ink by Chameleon Optics, Inc. of Bethlehem, Pa. Other suitable forms that electro-chromic material may take, as well as various other ways in which electro-chromic material may be incorporated into the surgical tool 600, will be apparent to those of ordinary skill in the art in view of the teachings herein.

Figure 10A:
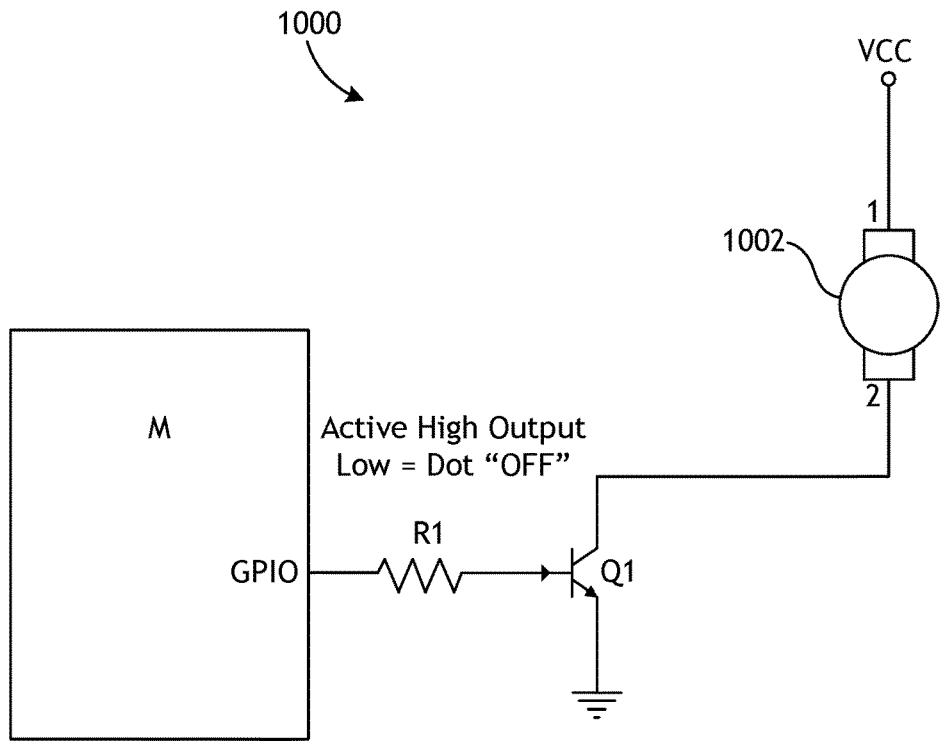
FIGS. 10A-10B are circuit diagrams of the surgical tool of FIG. 6 for activating an alternate indicator, according to one or more embodiments.
Figure 10B:
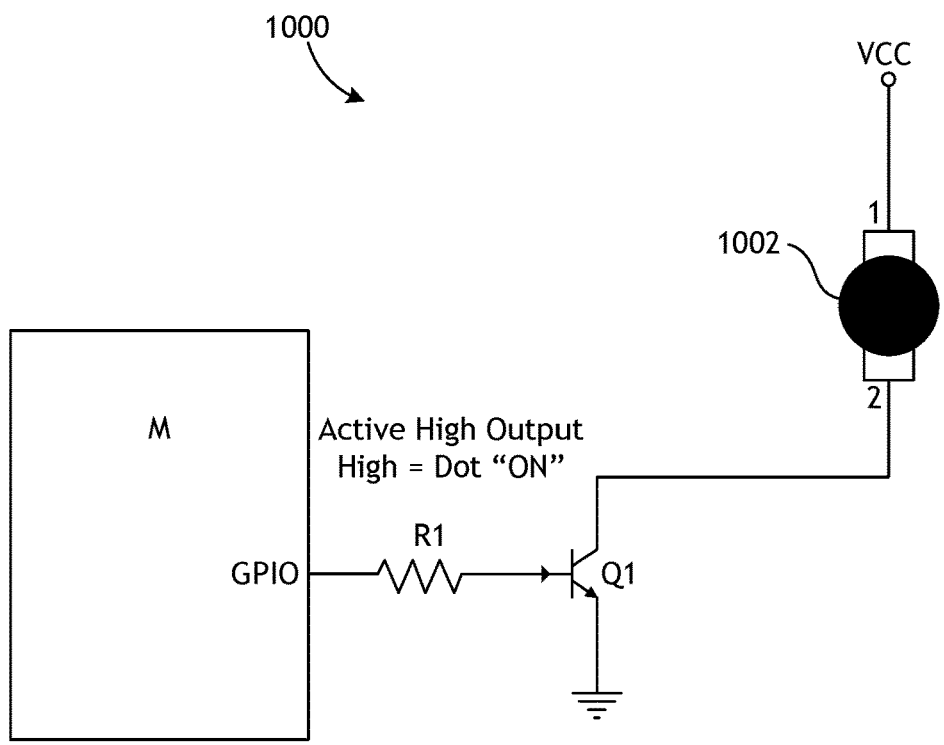

The surgical tool 600 may include electronic systems for controlling activation of the electro-chromic indicator. FIG. 10A and FIG. 10B illustrate an exemplary control circuit 1000 for an electro-chromic indicator 1002, according to one or more embodiments. The control circuit 1000 includes a controller or microcontroller M that is electrically connected to the electro-chromic indicator 1002. The NFC circuitry may supply power to the microcontroller M via inductive power transfer as discussed above; however, other means may be utilized to power the microcontroller M, such as a capacitor, battery, electrical connection, etc. The microcontroller M powers the electro-chromic indicator 1002 based on instructions that the microcontroller M receives from the robotic surgical system (e.g., the robotic manipulator). For example, tool life information of the surgical tool 600 is uploaded to the robotic surgical system 100 when the surgical tool 600 is loaded into the carriage of the robotic manipulator, and, if criteria is met that defines one procedure use of the surgical tool 600, the number of uses is incremented by one and downloaded from the robotic surgical system 100 to a memory of the surgical tool 600. If the robotic surgical system 100 determines that the end of life of the surgical tool 600 is met (i.e., that the surgical tool 600 has expired) due to being incremented by one, the microcontroller M powers the circuitry to apply the appropriate voltage and current to the electro-chromic ink to change the electro-chromic indicator 1002 from a first color to a second color. In other examples, however, the control circuit 1000 is integrated within the robotic surgical system and/or the robotic manipulator, which determines expiration of the surgical tool 600 by measuring useful life (e.g., counting operations) via NFC protocols and RFID tags discussed above and directs the microcontroller M to send power to the electro-chromic indicator 1002 electrically connected thereto upon determining that the useful life of the surgical tool 600 has been exhausted. In these latter examples, the electro-chromic indicator 1002 may be included in a tool-side circuitry or PCB of the surgical tool 600 that electrically connects to the control circuit 1002 via wireless coupling as described above or via physical electrical connections. The voltage applied to the electro-chromic indicator 1002 changes the electro-chromic indicator 1002 from a first color to a second color.

FIG. 10A illustrates the electro-chromic indicator 1002 before voltage exposure has changed it from the first color to the second color, and FIG. 10B illustrates the electro-chromic indicator 1002 that has been changed to the second color after being exposed to voltage. In some examples, the electro-chromic indicator 1002 changes color, from clear to black; however, the electro-chromic indicator 1002 may be configured to change between different colors. Once exposed to voltage, the electro-chromic indicator 1002 will remain the second color even when power is not being supplied to the electro-chromic indicator 1002, and this color change will persist regardless of shock, vibration, temperature, power failure, etc. Thus, once the electro-chromic indicator 1002 has changed colors, no mechanical, electrical, or physical inputs will alter its changed status. In these examples, a power source such as a battery, a capacitor, or power from the robotic manipulator is utilized to change the color of the electro-chromic indicator 1002; however, after the electro-chromic indicator 1002 has changed from the first color to the second color, power need not be continuously supplied to the electro-chromic indicator 1002 for it to remain the second color.

In some embodiments, the indicator 620 of the surgical tool 600 may comprise a photo-chromic indicator activated or illuminated with a light source such as an ultra-violet ("UV") light (or UV LED). For example, a photo-chromic film may be placed (or layered) between a colored backer plate and a UV protective filter. The photo-chromic film is visible through the UV protective filter and, in some examples, the UV protective filter is clear. The photo-chromic film is clear before being exposed to UV light, but changes color (e.g., to red) when exposed to UV light. Also, the colored backer plate may be various colors that the user may view before activation of the photo-chromic film and, in one example, the colored backer plate is green. The UV protective filter, the photo-chromic film, and the colored backer plate are laminated together to form the photo-chromic indicator.

The photo-chromic indicator may be positioned on the housing 608 of the surgical tool 600 with the UV protective filter facing outward therefrom, as illustrated in FIG. 6. Since the UV protective filter is outward-facing, the user will be protected from UV exposure in examples where the light source is provided within the housing 608 and would otherwise emit UV light exterior to the housing 608 but for the UV protective filter shielding the user from UV light. The photo-chromic indicator is positioned sufficiently proximate to the UV light, such that the UV light may illuminate the photo-chromic indicator when the UV light is powered, thereby causing the photo-chromic film therein to change colors (e.g., from clear to red). In some examples, the UV light source is provided on the robotic surgical system 100, for example, on the robotic manipulator and/or the carriage thereof. Also, the change in color of the photo-chromic indicator may be time and intensity dependent. Thus, the coloring of the photo-chromic indicator may be accelerated by supplying more voltage, whereas, exposure time may be increased if additional input power is required. The photo-chromic indicator may be irreversible, such that the photo-chromic ink may not return to its original color after it has been activated to change color.

Figure 11A:
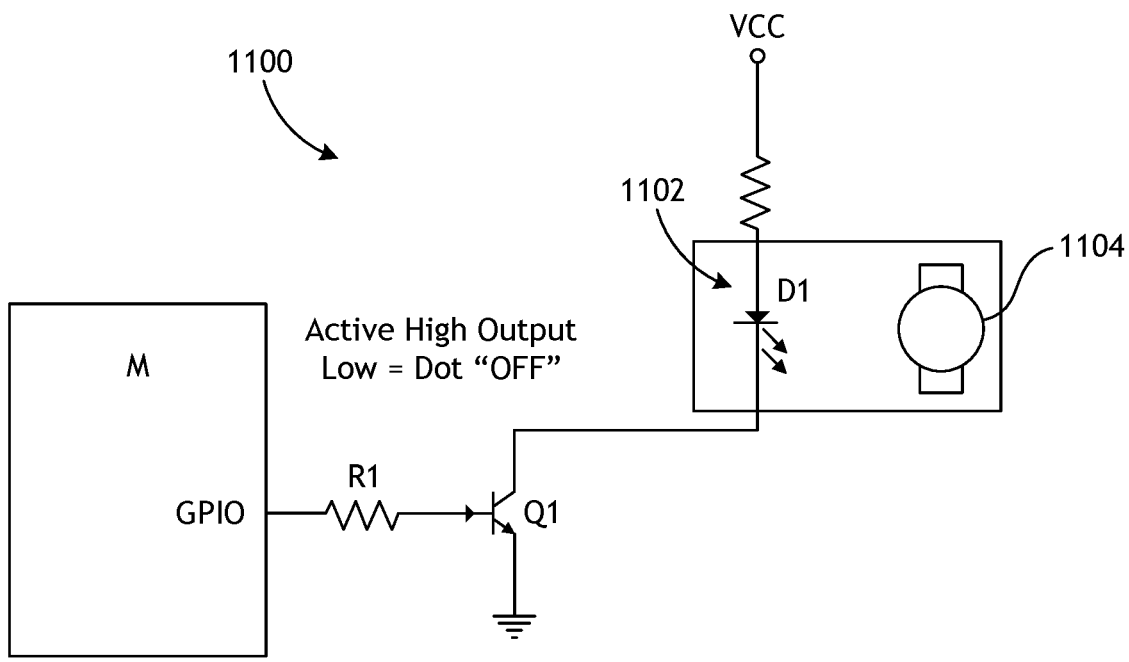
FIGS. 11A-11B are circuit diagrams of the surgical tool of FIG. 6 for activating an alternate indicator, according to one or more embodiments.
Figure 11B:
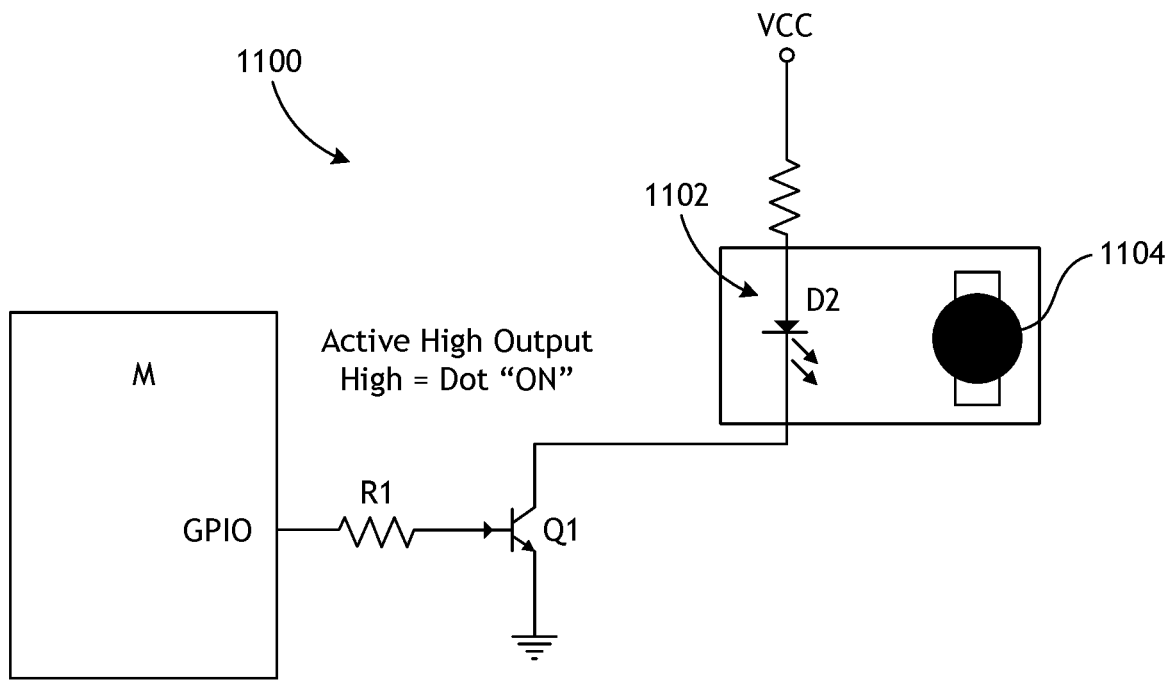

The surgical tool 600 may include electronic systems for controlling activation of the photo-chromic indicator. FIG. 11A and FIG. 11B illustrate an exemplary control circuit 1100 for controlling a UV light 1102 configured to activate a photo-chromic indicator 1104, according to one or more embodiments. The control circuit 1100 includes a microcontroller M that interfaces with the UV light 1102. The NFC circuitry may supply power to the microcontroller M via inductive power transfer; however, other means may be utilized to supply power to the microcontroller M, such as batteries, capacitors, electrical connections, etc. The microcontroller M powers the UV light 1102 based on instructions that the microcontroller M receives from the robotic surgical system (e.g., the robotic manipulator). For example, when the surgical tool 600 has expired, the microcontroller M powers the circuitry and the UV light 1102. When powered, the UV light 1102 emits UV light that changes the color of the photo-chromic indicator 1104 from clear to a second color. The UV light 1102 may utilize light pipes or other similar constructs to direct light emitted therefrom, such that the UV light 1102 need not be placed directly adjacent or proximate to the photo-chromic indicator 1104.

In some examples, the UV light 1102 and the control circuit 1100 are integrated within the robotic manipulator, whereas, in other examples, the UV light 1102 and the control circuit 1100 are integrated within the housing 608 of the surgical tool 600. Where the UV light 1102 and the control circuit 1100 are integrated within the robotic manipulator and/or the carriage, the robotic surgical system 100 may determine expiration of the surgical tool 600 by measuring useful life (e.g., counting operations) via NFC protocols and RFID tags, and updating or incrementing a memory of the surgical tool 600 with a newly calculated tool life, as discussed above; and then the microcontroller M directs power to the UV light 1102 upon determining that the useful life of the surgical tool 600 has been exhausted. In these examples, the UV light 1102 may be powered by robotic surgical system and/or the robotic manipulator. However, where the UV light 1102 and the control circuit 1100 are integrated within the surgical tool 600, the microcontroller M may power the UV light 1102 when directed by the robotic surgical system 100, or depending on the input voltage $V_{in}$ supplied by the robotic manipulator/robotic surgical system as discussed above (e.g., via a difference in the first input voltage $V_{in}^1$ and the second input voltage $V_{in}^2$). In these latter examples, a variety of means may be utilized to power the UV light 1102, including the inductive and/or capacitive power transfer detailed above, batteries, electrical connections, mechanical drive inputs, etc.

FIG. 11A illustrates the photo-chromic indicator 1104 that changes from a first state to a second state when acted upon by an energy input. The first and second states may be various colors, patterns, or combinations, or the same. In one example, the photo-chromic indicator 1104 is clear when in the first state before being exposed to UV light, such that the color (e.g., green) of the colored backer plate is visible to the user through the clear photo-chromic film layer, but is colored (e.g., red) when changed to its second state via UV exposure, such that the second state color is visible to the user. FIG. 11B illustrates the photo-chromic indicator 1104 that has transitioned into the second state after having been subject to UV exposure via the UV light 1102. It will be appreciated, however, that photo-chromic indicator 1104 may be configured to change between different colors and/or patterns. Once exposed to UV light, the photo-chromic indicator 1104 will remain colored even when power is not being supplied to the UV light 1102, and this color change will persist regardless of shock, vibration, temperature, power failure, etc. In these examples, energy is initially needed to change the photo-chromic indicator 1104 from the first state to the second state but, after changing states, energy is not subsequently needed for the photo-chromic indicator 1104 to remain in the second state.

In some examples, two or more of the indicators 620 are utilized. In these examples, the two or more indicators 620 may be of the same or different type. For example, the two or more indicators 620 may include a pair of LED indicators, a pair of electro-chromic indicators, or a pair of photo-chromic indicators. In other examples, the two or more indicators 620 include at least one LED indicator and at least one electro-chromic indicator, or at least one LED indicator and at least one photo-chromic indicator, or at least one electro-chromic indicator and at least one photo-chromic indicator. In even other examples, three or more indicators 620 are utilized. For example, the three or more indicators 620 may include at least one LED indicator, at least one electro-chromic indicator, and at least one photo-chromic indicator.

In addition to or in lieu of using any combination of the foregoing LED indicators, electro-chromic indicators, photo-chromic indicators, or combination thereof, the indicator 620 may comprise a thermo-chromic indicator configured to change state in response to an increase in temperature. For instance, before utilizing the surgical tool 600, the thermo-chromic indicator may be black and then turn red or some other color after the surgical tool 600 is used or after the surgical tool 600 has reached its useful life. Various suitable kinds of materials and combinations of materials that may be used to form the thermo-chromic indicator will be apparent to those of ordinary skill in the art in view of the teachings herein. Here, the thermo-chromic indicator may comprise a thermo-chromic material. In some examples, the thermo-chromic material is coupled with one or more features within the housing 608 (FIG. 6) that are electrically activated during use of the surgical tool 600. For example, a resistor may be used to generate heat in response to electrical activation of components during use of the surgical tool 600. Other suitable ways in which thermo-chromic material may be heated due to use of the surgical tool 600 will be apparent to those of ordinary skill in the art in view of the teachings herein.

It should also be understood that some versions of thermo-chromic material may be configured to maintain a changed color even after the temperature falls back to a level where it was before utilization of the surgical tool 600. For instance, before the surgical tool 600 is used, thermo-chromic material may be black. When thermo-chromic material is heated in response to use of the surgical tool 600, thermo-chromic material changes red (or some other color). After use of the surgical tool 600 and thermo-chromic material cools back down to the same temperature it was at before use, the color of thermo-chromic material may remain red (or some other color indicating use). By way of example, thermo-chromic material may comprise a thermo-chromic material by LCR Hallcrest of Glenview, Ill. Other suitable forms that thermo-chromic material may take, as well as various other ways in which thermo-chromic material may be incorporated into the surgical tool 600, will be apparent to those of ordinary skill in the art in view of the teachings herein.

In addition to or in lieu of using any combination of the foregoing LED indicators, electro-chromic indicators, photo-chromic indicators, thermo-chromic indicators, or combination thereof, the indicator 620 may comprise a flip dot indicator. The flip dot indicator may include a single dot or a matrix of dots. Regardless of number, the dots each have a first side with a first color and a second side with a second color. The flip dot indicator displays the first side with the first color when no power is applied, but upon application of power, the dots flip sides to expose the second side's second color. In some examples, the flip dot indicator is coupled with one or more features within the housing 608 (FIG. 6) that are electrically activated during use of the surgical tool 600, and various means may be utilized to power the flip dot indicator when triggered. For example, a trickle-charging capacitor, an internal battery, or combinations of the same may be used to power the flip dot indicator when activated. Other suitable ways in which flip dot indicator may be powered will be apparent to those of ordinary skill in the art in view of the teachings herein.

Embodiments disclosed herein include:

A. A surgical tool for a robotic surgical system, the surgical tool including a tool housing having a mounting portion for releasably securing the surgical tool to a carriage of the robotic surgical system, tool circuitry included in the tool housing, and an indicator electrically connected to the tool circuitry, wherein the indicator is activated when the tool circuitry couples with a corresponding circuitry of the robotic surgical system.

B. A method of indicating tool life of a surgical tool utilizable with a robotic surgical system, the method including mounting a tool housing of the surgical tool to a carriage of the robotic surgical system, inductively coupling a tool circuitry of the surgical tool with a corresponding circuitry of the robotic surgical system to thereby generate power in the tool circuitry, harvesting power from the robotic surgical system with the tool circuitry when the tool housing is mounted to the carriage, and activating an indicator connected to the tool circuitry using power generated in the tool circuitry.

Each of embodiments A and B may have one or more of the following additional elements in any combination: Element 1: wherein the mounting portion includes a mounting surface that abuts a sterile barrier separating the surgical tool and the robotic surgical system when the tool housing is mounted in the carriage and, when the tool housing is mounted in the carriage, an inductor of the robotic surgical system couples with an inductor of the surgical tool wirelessly through the mounting surface of the tool housing. Element 2: wherein the indicator is selected from the group consisting of an LED light source, an electro-chromic material, a photo-chromic material, and a thermo-chromic material, and any combination thereof. Element 3: wherein the tool circuitry includes a capacitor that is inductively charged by coupling the tool circuitry to the corresponding circuitry. Element 4: wherein power induced via coupling of the tool circuitry and corresponding circuitry charges the capacitor during a final use of the surgical tool. Element 5: wherein uncoupling the tool circuitry and the corresponding circuitry discharges the capacitor of the surgical tool to illuminate the indicator. Element 6: wherein the tool circuitry discharges the capacitor to illuminate the indicator when coupled to the corresponding circuitry of the robotic surgical system. Element 7: wherein the indicator is obstructed from view when the tool housing is mounted within the carriage. Element 8: wherein power induced via coupling of the tool circuitry and the corresponding circuitry of the robotic surgical system charges the capacitor during a final use of the surgical tool and during at least one preceding use of the surgical tool before the final use. Element 9: wherein the tool circuitry further includes a capacitor and a first inductor connected to the indicator, wherein power induced via coupling of the first inductor and a second inductor associated with the corresponding circuit of the robotic surgical system charges the capacitor during a final use of the surgical tool. Element 10: wherein power induced via coupling of the first inductor and the second inductor builds charge in the capacitor during at least one preceding use of the surgical tool before the final use. Element 11: wherein the indicator includes an electro-chromic material that changes state when exposed to voltage, wherein the tool circuitry includes a controller that directs voltage to the electro-chromic material based on instructions indicative of tool life. Element 12: wherein the controller directs voltage to the electro-chromic material during or after a final use of the surgical tool. Element 13: wherein coupling of the tool circuitry and the corresponding circuitry of the robotic surgical system induces power in the tool circuitry that powers the controller. Element 14: wherein the indicator comprises a photo-chromic material that changes state when activated by a light source, wherein the light source emits a light that interacts with the photo-chromic material and thereby causes the photo-chromic material to change state. Element 15: wherein the tool circuitry includes a controller that triggers the light source to emit light on the electro-chromic material when a useful life of the surgical tool is reached or exhausted. Element 16: wherein the light source is provided within the carriage of the robotic surgical system or within the tool housing of the surgical tool, and wherein, when the light source is provided within the carriage of the robotic surgical system, the robotic surgical system supplies power to the light source. Element 17: wherein the circuitry includes a capacitor that is connected to the indicator, the method further comprising the charging the capacitor when the tool circuitry and the corresponding circuitry are inductively coupled. Element 18: wherein activating the indicator includes discharging the capacitor to power the indicator.

By way of non-limiting example, exemplary combinations applicable to A and B include: Element 3 with Element 4; Element 4 with Element 5; Element 4 with Element 6; Element 6 with Element 7; Element 3 with Element 8; Element 9 with Element 10; Element 11 with Element 12; Element 11 with Element 13; Element 14 with Element 15; Element 14 with Element 16; and Element 17 with Element 18.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:
1. A surgical tool for a robotic surgical system, the surgical tool comprising:
a tool housing having a mounting portion for releasably securing the surgical tool to a carriage of the robotic surgical system;

tool circuitry included in the tool housing and configured to communicate with corresponding circuitry of the robotic surgical system; and an indicator provided on the tool housing and electrically connected to the tool circuitry, the tool circuitry including a capacitor and a first inductor connected to the indicator, wherein power induced via coupling of the first inductor and a second inductor associated with the corresponding circuit of the robotic surgical system charges the capacitor during a final use of the surgical tool, and wherein the indicator is activatable upon communicably coupling the tool circuitry with the corresponding circuitry of the robotic surgical system, and the indicator provides a visual indication of remaining useful life of the surgical tool.

2. The surgical tool of claim 1, wherein the mounting portion includes a mounting surface that abuts a sterile barrier separating the surgical tool and the robotic surgical system when the tool housing is mounted in the carriage and, when the tool housing is mounted in the carriage, an inductor of the robotic surgical system couples with an inductor of the surgical tool wirelessly through the mounting surface of the tool housing.

3. The surgical tool of claim 1, wherein the indicator is selected from the group consisting of an LED light source, an electro-chromic material, a photo-chromic material, and a thermo-chromic material, and any combination thereof.

4. The surgical tool of claim 1, wherein the capacitor is inductively charged by coupling the tool circuitry to the corresponding circuitry.

5. The surgical tool of claim 4, wherein power induced via coupling of the tool circuitry and corresponding circuitry charges the capacitor during the final use of the surgical tool.

6. The surgical tool of claim 5, wherein uncoupling the tool circuitry and the corresponding circuitry discharges the capacitor of the surgical tool to illuminate the indicator.

7. The surgical tool of claim 5, wherein the tool circuitry discharges the capacitor to illuminate the indicator when coupled to the corresponding circuitry of the robotic surgical system.

8. The surgical tool of claim 7, wherein the indicator is obstructed from view when the tool housing is mounted within the carriage.

9. The surgical tool of claim 4, wherein power induced via coupling of the tool circuitry and the corresponding circuitry of the robotic surgical system charges the capacitor during at least one preceding use of the surgical tool before the final use.

10. The surgical tool of claim 1, wherein power induced via coupling of the first inductor and the second inductor builds charge in the capacitor during at least one preceding use of the surgical tool before the final use.

11. The surgical tool of claim 1, wherein the indicator includes an electro-chromic material that changes state when exposed to voltage, wherein the tool circuitry includes a controller that directs voltage to the electro-chromic material based on instructions indicative of the remaining useful life of the surgical tool.

12. The surgical tool of claim 11, wherein the controller directs voltage to the electro-chromic material during or after a final use of the surgical tool.

13. The surgical tool of claim 11, wherein coupling of the tool circuitry and the corresponding circuitry of the robotic surgical system induces power in the tool circuitry that powers the controller.

14. The surgical tool of claim 1, wherein the indicator comprises a photo-chromic material that changes state when activated by a light source, wherein the light source emits a light that interacts with the photo-chromic material and thereby causes the photo-chromic material to change state.

15. The surgical tool of claim 14, wherein the tool circuitry includes a controller that triggers the light source to emit light on the electro-chromic material when the remaining useful life of the surgical tool is reached or exhausted.

16. The surgical tool of claim 14, wherein the light source is provided within the carriage of the robotic surgical system or within the tool housing of the surgical tool; and wherein, when the light source is provided within the carriage of the robotic surgical system, the robotic surgical system supplies power to the light source.

17. A method of indicating tool life of a surgical tool utilizable with a robotic surgical system, the method comprising:

mounting a tool housing of the surgical tool to a carriage of the robotic surgical system;

inductively coupling a tool circuitry of the surgical tool with a corresponding circuitry of the robotic surgical system, the tool circuitry including a capacitor and a first inductor connected to an indicator provided on the tool housing and connected to the tool circuitry;

generating power in the tool circuitry by inductively coupling the first inductor and a second inductor associated with the corresponding circuit of the robotic surgical system and thereby charging the capacitor during a final use of the surgical tool;

harvesting power from the robotic surgical system with the tool circuitry when the tool housing is mounted to the carriage, and thereby powering the indicator; and activating the indicator to provide a visual indication of remaining useful life of the surgical tool.

18. The method of claim 17, wherein activating the indicator includes discharging the capacitor to power the indicator.

* * * * *